United States Patent
Brewer et al.

(10) Patent No.: US 10,716,895 B2
(45) Date of Patent: Jul. 21, 2020

(54) INFUSION PUMP SYSTEM AND METHOD

(71) Applicant: Bigfoot Biomedical, Inc., Milpitas, CA (US)

(72) Inventors: Tracy Brewer, Hayward, CA (US); Wenkang Qi, Cupertino, CA (US); Johannes T. VandenCrommenacker, Cupertino, CA (US)

(73) Assignee: BIGFOOT BIOMEDICAL, INC., Milpitas, CA (US)

( * ) Notice: Subject to any disclaimer, the term of this patent is extended or adjusted under 35 U.S.C. 154(b) by 372 days.

(21) Appl. No.: 15/240,208

(22) Filed: Aug. 18, 2016

(65) Prior Publication Data

US 2016/0354544 A1    Dec. 8, 2016

Related U.S. Application Data

(63) Continuation of application No. 13/908,513, filed on Jun. 3, 2013, now Pat. No. 9,446,187.

(51) Int. Cl.
*A61M 5/00*  (2006.01)
*A61M 5/172* (2006.01)
(Continued)

(52) U.S. Cl.
CPC ...... *A61M 5/1723* (2013.01); *A61M 5/14244* (2013.01); *A61M 5/14248* (2013.01);
(Continued)

(58) Field of Classification Search
CPC .... A61M 2005/14264; A61M 2205/18; A61M 2205/3372; A61M 2205/52; A61M 5/14244; A61M 5/16831; A61M 5/172; A61M 2005/14268; A61M 5/1413; A61M 2005/14208; A61M 2005/14573; A61F 13/42
See application file for complete search history.

(56) References Cited

U.S. PATENT DOCUMENTS 4,619,653 A    10/1986   Fischell
4,784,645 A    11/1988   Fischell
(Continued)

FOREIGN PATENT DOCUMENTS

CA    2543545        5/2005
DE    196 27 619 A   1/1998
(Continued)

OTHER PUBLICATIONS

Asante Pearl, Insulin Pump User Manual, 2012, 180 pages.
(Continued)

*Primary Examiner* — Scott J Medway
(74) *Attorney, Agent, or Firm* — Hamre, Shumann, Mueller & Larson, P.C.

(57) ABSTRACT

Some embodiments of an infusion pump system may be configured to detect when at least one component of the pump system is exposed to a moisture level above a threshold level. In particular embodiments, the infusion pump system can be equipped with a moisture level detection system that can sense when a moisture level above the threshold level has occurred to the pump device, which thereby enables the infusion pump system to initiate one or more patient safety countermeasures.

17 Claims, 9 Drawing Sheets

(51) Int. Cl.
  *A61M 5/142* (2006.01)
  *A61M 5/145* (2006.01)
  *A61M 5/168* (2006.01)
  *A61M 5/162* (2006.01)
  *A61M 5/50* (2006.01)

(52) U.S. Cl.
  CPC ........ *A61M 5/14566* (2013.01); *A61M 5/162* (2013.01); *A61M 5/16831* (2013.01); *A61M 5/50* (2013.01); *A61M 2005/14264* (2013.01); *A61M 2205/02* (2013.01); *A61M 2205/3379* (2013.01); *A61M 2205/44* (2013.01); *A61M 2205/502* (2013.01); *A61M 2205/587* (2013.01); *A61M 2205/8206* (2013.01)

(56) References Cited

U.S. PATENT DOCUMENTS

| | | | |
|---|---|---|---|
| 5,537,095 A * | 7/1996 | Dick | A61F 5/48 128/886 |
| 5,685,844 A | 11/1997 | Martilla | |
| 5,838,240 A * | 11/1998 | Johnson | A61F 5/48 340/604 |
| 5,903,222 A * | 5/1999 | Kawarizadeh | G01N 27/223 128/886 |
| 6,126,595 A | 10/2000 | Amano | |
| 6,233,471 B1 | 5/2001 | Berner et al. | |
| 6,461,331 B1 | 10/2002 | Van Antwerp | |
| 6,474,219 B2 | 11/2002 | Klitmose et al. | |
| 6,485,461 B1 | 11/2002 | Mason et al. | |
| 6,508,788 B2 | 1/2003 | Preuthun | |
| 6,524,280 B2 | 2/2003 | Hansen et al. | |
| 6,533,183 B2 | 3/2003 | Aasmul et al. | |
| 6,537,251 B2 | 3/2003 | Klitmose | |
| 6,540,672 B1 | 4/2003 | Simonsen et al. | |
| 6,544,229 B1 | 4/2003 | Danby et al. | |
| 6,547,764 B2 | 4/2003 | Larsen et al. | |
| 6,551,276 B1 | 4/2003 | Mann et al. | |
| 6,554,798 B1 | 4/2003 | Mann et al. | |
| 6,554,800 B1 | 4/2003 | Nezhadian et al. | |
| 6,558,320 B1 | 5/2003 | Causey, III et al. | |
| 6,558,351 B1 | 5/2003 | Steil et al. | |
| 6,562,001 B2 | 5/2003 | Lebel et al. | |
| 6,562,011 B1 | 5/2003 | Buch-Rasmussen et al. | |
| 6,564,105 B2 | 5/2003 | Starkweather et al. | |
| 6,569,126 B1 | 5/2003 | Poulsen et al. | |
| 6,571,128 B2 | 5/2003 | Lebel et al. | |
| 6,572,542 B1 | 6/2003 | Houben | |
| 6,577,899 B2 | 6/2003 | Lebel et al. | |
| 6,582,404 B1 | 6/2003 | Klitgaard et al. | |
| 6,585,644 B2 | 7/2003 | Lebel et al. | |
| 6,585,699 B2 | 7/2003 | Ljunggreen et al. | |
| 6,595,956 B1 | 7/2003 | Gross et al. | |
| 6,605,067 B1 | 8/2003 | Larsen | |
| 6,613,019 B2 | 9/2003 | Munk | |
| 6,641,533 B2 | 11/2003 | Causey, III et al. | |
| 6,648,821 B2 | 11/2003 | Lebel et al. | |
| 6,650,951 B1 | 11/2003 | Jones et al. | |
| 6,656,158 B2 | 12/2003 | Mahoney et al. | |
| 6,656,159 B2 | 12/2003 | Flaherty | |
| 6,659,948 B2 | 12/2003 | Lebel et al. | |
| 6,659,978 B1 | 12/2003 | Kasuga et al. | |
| 6,659,980 B2 | 12/2003 | Moberg et al. | |
| 6,663,602 B2 | 12/2003 | Møller | |
| 6,668,196 B1 | 12/2003 | Villegas et al. | |
| 6,669,669 B2 | 12/2003 | Flaherty et al. | |
| 6,687,546 B2 | 2/2004 | Lebel et al. | |
| 6,690,192 B1 | 2/2004 | Wing | |
| 6,691,043 B2 | 2/2004 | Ribeiro, Jr. | |
| 6,692,457 B2 | 2/2004 | Flaherty | |
| 6,692,472 B2 | 2/2004 | Hansen et al. | |
| 6,694,191 B2 | 2/2004 | Starkweather et al. | |
| 6,699,218 B2 | 3/2004 | Flaherty et al. | |
| 6,702,779 B2 | 3/2004 | Connelly et al. | |
| 6,715,516 B2 | 4/2004 | Ohms et al. | |
| 6,716,198 B2 | 4/2004 | Larsen | |
| 6,723,072 B2 | 4/2004 | Flaherty et al. | |
| 6,723,077 B2 | 4/2004 | Pickup et al. | |
| 6,733,446 B2 | 5/2004 | Lebel et al. | |
| 6,736,796 B2 | 5/2004 | Shekalim | |
| 6,740,059 B2 | 5/2004 | Flaherty | |
| 6,740,072 B2 | 5/2004 | Starkweather et al. | |
| 6,740,075 B2 | 5/2004 | Lebel et al. | |
| 6,744,350 B2 | 6/2004 | Blomquist | |
| 6,749,587 B2 | 6/2004 | Flaherty | |
| 6,752,787 B1 | 6/2004 | Causey, III et al. | |
| 6,758,810 B2 | 7/2004 | Lebel et al. | |
| 6,768,425 B2 | 7/2004 | Flaherty et al. | |
| 6,780,156 B2 | 8/2004 | Haueter et al. | |
| 6,786,246 B2 | 9/2004 | Ohms et al. | |
| 6,786,890 B2 | 9/2004 | Preuthun et al. | |
| 6,796,957 B2 | 9/2004 | Carpenter et al. | |
| 6,796,970 B1 | 9/2004 | Klitmose et al. | |
| 6,799,149 B2 | 9/2004 | Hartlaub | |
| 6,809,653 B1 | 10/2004 | Mann et al. | |
| 6,810,290 B2 | 10/2004 | Lebel et al. | |
| 6,811,533 B2 | 11/2004 | Lebel et al. | |
| 6,811,534 B2 | 11/2004 | Bowman, IV et al. | |
| 6,813,519 B2 | 11/2004 | Lebel et al. | |
| 6,827,702 B2 | 12/2004 | Lebel et al. | |
| 6,830,558 B2 | 12/2004 | Flaherty et al. | |
| 6,852,104 B2 | 2/2005 | Blomquist | |
| 6,854,620 B2 | 2/2005 | Ramey | |
| 6,854,653 B2 | 2/2005 | Eilersen | |
| 6,855,129 B2 | 2/2005 | Jensen et al. | |
| 6,872,200 B2 | 3/2005 | Mann et al. | |
| 6,873,268 B2 | 3/2005 | Lebel et al. | |
| 6,878,132 B2 | 4/2005 | Kipfer | |
| 6,893,415 B2 | 5/2005 | Madsen et al. | |
| 6,899,695 B2 | 5/2005 | Herrera | |
| 6,899,699 B2 | 5/2005 | Enggaard | |
| 6,922,590 B1 | 7/2005 | Whitehurst | |
| 6,936,006 B2 | 8/2005 | Sabra | |
| 6,936,029 B2 | 8/2005 | Mann et al. | |
| 6,945,961 B2 | 9/2005 | Miller et al. | |
| 6,948,918 B2 | 9/2005 | Hansen | |
| 6,950,708 B2 | 9/2005 | Bowman, IV et al. | |
| 6,960,192 B1 | 11/2005 | Flaherty et al. | |
| 6,979,326 B2 | 12/2005 | Mann et al. | |
| 6,997,911 B2 | 2/2006 | Klitmose | |
| 6,997,920 B2 | 2/2006 | Mann et al. | |
| 7,005,078 B2 | 2/2006 | Van Lintel et al. | |
| 7,008,399 B2 | 3/2006 | Larson et al. | |
| 7,014,625 B2 | 3/2006 | Bengtsson | |
| 7,018,360 B2 | 3/2006 | Flaherty et al. | |
| 7,025,743 B2 | 4/2006 | Mann | |
| 7,029,455 B2 | 4/2006 | Flaherty | |
| 7,054,836 B2 | 5/2006 | Christensen et al. | |
| 7,104,972 B2 | 9/2006 | Møller et al. | |
| 7,128,727 B2 | 10/2006 | Flaherty et al. | |
| 7,133,329 B2 | 11/2006 | Skyggebjerg et al. | |
| 7,232,423 B2 | 6/2007 | Mernoe et al. | |
| 7,645,272 B2 | 1/2010 | Chang et al. | |
| 7,686,787 B2 | 3/2010 | Moberg et al. | |
| 7,704,227 B2 | 4/2010 | Moberg et al. | |
| 7,875,022 B2 | 1/2011 | Wenger et al. | |
| 8,088,120 B2 | 1/2012 | Worsoff | |
| 8,100,852 B2 | 1/2012 | Moberg et al. | |
| 8,454,562 B1 | 6/2013 | Sims | |
| 8,585,635 B2 | 11/2013 | Degen et al. | |
| 9,780,554 B2 * | 10/2017 | Kardassakis | G08B 21/20 |
| 2001/0056262 A1 | 12/2001 | Cabiri | |
| 2002/0004651 A1 | 1/2002 | Ljndggreen et al. | |
| 2002/0007154 A1 | 1/2002 | Hansen et al. | |
| 2002/0040208 A1 | 4/2002 | Flaherty et al. | |
| 2002/0070864 A1 * | 6/2002 | Jeutter | A61F 13/42 340/573.1 |
| 2002/0070868 A1 * | 6/2002 | Jeutter | G06K 19/0716 340/604 |
| 2002/0091358 A1 | 7/2002 | Klitmose | |
| 2002/0126036 A1 | 9/2002 | Flaherty et al. | |
| 2003/0055380 A1 | 3/2003 | Flaherty | |
| 2003/0065308 A1 | 4/2003 | Lebel et al. | |
| 2003/0088238 A1 | 5/2003 | Poulsen | |

(56) References Cited

U.S. PATENT DOCUMENTS

| | | |
|---|---|---|
| 2003/0093031 A1 | 5/2003 | Long et al. |
| 2003/0104982 A1 | 6/2003 | Wittmann et al. |
| 2003/0199825 A1 | 10/2003 | Flaherty |
| 2003/0216683 A1 | 11/2003 | Shekalim |
| 2004/0010207 A1 | 1/2004 | Flaherty et al. |
| 2004/0019325 A1 | 1/2004 | Shekalim |
| 2004/0064088 A1 | 4/2004 | Gorman et al. |
| 2004/0064096 A1 | 4/2004 | Flaherty et al. |
| 2004/0073175 A1 | 4/2004 | Jacobson et al. |
| 2004/0078028 A1 | 4/2004 | Flaherty et al. |
| 2004/0087894 A1 | 5/2004 | Flaherty |
| 2004/0092865 A1 | 5/2004 | Flaherty et al. |
| 2004/0092878 A1 | 5/2004 | Flaherty |
| 2004/0116866 A1 | 6/2004 | Gorman et al. |
| 2004/0127844 A1 | 7/2004 | Flaherty |
| 2004/0153032 A1 | 8/2004 | Garribotto et al. |
| 2004/0171983 A1 | 9/2004 | Sparks et al. |
| 2004/0176727 A1 | 9/2004 | Shekalim |
| 2004/0204673 A1 | 10/2004 | Flaherty |
| 2004/0220551 A1 | 11/2004 | Flaherty et al. |
| 2004/0235446 A1 | 11/2004 | Flaherty et al. |
| 2004/0260233 A1 | 12/2004 | Garibotto et al. |
| 2005/0021005 A1 | 1/2005 | Flaherty et al. |
| 2005/0022274 A1 | 1/2005 | Campbell et al. |
| 2005/0033250 A1* | 2/2005 | Collette ............... A61F 13/42 |
| | | 604/361 |
| 2005/0065760 A1 | 3/2005 | Murtfeldt et al. |
| 2005/0090808 A1 | 4/2005 | Malave et al. |
| 2005/0095063 A1 | 5/2005 | Fathallah |
| 2005/0160858 A1 | 7/2005 | Mernoe |
| 2005/0171512 A1 | 8/2005 | Flaherty |
| 2005/0182366 A1 | 8/2005 | Vogt et al. |
| 2005/0192561 A1 | 9/2005 | Mernoe |
| 2005/0203461 A1 | 9/2005 | Flaherty et al. |
| 2005/0215982 A1 | 9/2005 | Malave et al. |
| 2005/0222645 A1 | 10/2005 | Malave et al. |
| 2005/0238507 A1 | 10/2005 | DiIanni et al. |
| 2005/0245878 A1 | 11/2005 | Mernoe et al. |
| 2005/0251097 A1 | 11/2005 | Mernoe |
| 2005/0267402 A1 | 12/2005 | Stewart et al. |
| 2005/0273059 A1 | 12/2005 | Mernoe et al. |
| 2006/0041229 A1 | 2/2006 | Garibotto et al. |
| 2006/0069382 A1 | 3/2006 | Pedersen |
| 2006/0074381 A1 | 4/2006 | Malave et al. |
| 2006/0095014 A1 | 5/2006 | Ethelfeld |
| 2006/0135913 A1 | 6/2006 | Ethelfeld |
| 2006/0142698 A1 | 6/2006 | Ethelfeld |
| 2006/0178633 A1 | 8/2006 | Garibotto et al. |
| 2006/0184119 A1 | 8/2006 | Remde et al. |
| 2006/0200073 A1 | 9/2006 | Radmer et al. |
| 2006/0206054 A1 | 9/2006 | Shekalim |
| 2006/0247581 A1 | 11/2006 | Pedersen et al. |
| 2006/0264889 A1 | 11/2006 | Moberg et al. |
| 2006/0271020 A1 | 11/2006 | Huang et al. |
| 2007/0073228 A1 | 3/2007 | Mernoe et al. |
| 2007/0073235 A1 | 3/2007 | Estes et al. |
| 2007/0073236 A1 | 3/2007 | Mernoe et al. |
| 2007/0124002 A1 | 5/2007 | Estes et al. |
| 2007/0156092 A1 | 7/2007 | Estes et al. |
| 2007/0167905 A1 | 7/2007 | Estes et al. |
| 2007/0167912 A1 | 7/2007 | Causey et al. |
| 2007/0227534 A1 | 10/2007 | Nobutani et al. |
| 2007/0252713 A1* | 11/2007 | Rondoni ............... A61B 5/202 |
| | | 340/573.5 |
| 2008/0022998 A1 | 1/2008 | Hamano et al. |
| 2008/0125700 A1 | 5/2008 | Moberg et al. |
| 2008/0154187 A1 | 6/2008 | Krulevitch et al. |
| 2008/0172027 A1 | 7/2008 | Blomquist |
| 2008/0188837 A1 | 8/2008 | Belsky et al. |
| 2008/0306444 A1 | 12/2008 | Brister |
| 2009/0076453 A1 | 3/2009 | Mejlhede et al. |
| 2009/0126463 A1 | 5/2009 | Friedli et al. |
| 2010/0058835 A1 | 3/2010 | Seo |
| 2010/0198187 A1 | 8/2010 | Yodfat et al. |
| 2012/0116197 A1 | 5/2012 | Moberg et al. |
| 2013/0053820 A1 | 2/2013 | Estes et al. |
| 2013/0209315 A1* | 8/2013 | Kimura ............... G01N 25/4826 |
| | | 422/88 |
| 2015/0268182 A1* | 9/2015 | Wettstein ........... G01N 25/4833 |
| | | 374/13 |

FOREIGN PATENT DOCUMENTS

| | | |
|---|---|---|
| DE | 102 36 669 | 2/2004 |
| DE | 20 2005 012 358 | 10/2005 |
| EP | 0 496 141 | 7/1992 |
| EP | 0 612 004 | 8/1994 |
| EP | 0 580 723 | 10/1995 |
| EP | 1 045 146 | 10/2000 |
| EP | 1 136 698 | 9/2001 |
| EP | 1 177 802 | 2/2002 |
| EP | 0 721 358 | 5/2002 |
| EP | 1 495 775 | 1/2005 |
| EP | 1 527 792 | 5/2005 |
| EP | 1 754 498 | 2/2007 |
| FR | 2 585 252 | 1/1987 |
| GB | 747 701 | 4/1956 |
| GB | 2 218 831 | 11/1989 |
| WO | WO 1990/015928 | 12/1990 |
| WO | WO 1997/021457 | 6/1997 |
| WO | WO 1998/011927 | 3/1998 |
| WO | WO 1998/057683 | 12/1998 |
| WO | WO 1999/021596 | 5/1999 |
| WO | WO 1999/039118 | 8/1999 |
| WO | WO 1999/048546 | 9/1999 |
| WO | WO 2001/072360 | 10/2001 |
| WO | WO 2001/091822 | 12/2001 |
| WO | WO 2001/091833 | 12/2001 |
| WO | WO 2002/040083 | 5/2002 |
| WO | WO 2002/057627 | 7/2002 |
| WO | WO 2002/100469 | 12/2002 |
| WO | WO 2003/103763 | 12/2003 |
| WO | WO 2004/056412 | 7/2004 |
| WO | WO 2004/093648 | 11/2004 |
| WO | WO 2004/110526 | 12/2004 |
| WO | WO 2005/002652 | 1/2005 |
| WO | WO 2005/039673 | 5/2005 |
| WO | WO 2005/072794 | 8/2005 |
| WO | WO 2005/072795 | 8/2005 |
| WO | WO 2006/075016 | 7/2006 |
| WO | WO 2006/105792 | 10/2006 |
| WO | WO 2006/105793 | 10/2006 |
| WO | WO 2006/105794 | 10/2006 |

OTHER PUBLICATIONS

Collins and Lee, "Microfluidic flow transducer based on the measurement of electrical admittance," Lab Chip, 2003, 12 pages.
Debiotech News Release, "Debiotech reveals its new miniaturized Disposable Insulin Nanopump™ for Diabetes therapy," available at http://www.debiotech.com/news/nw_159.html Apr. 24, 2006, 3 pages.
International Search Report and Written Opinion in International Application No. US2014/040544, dated Oct. 31, 2014, 2 pages.
Medtronic News Release, "Medtronic Receives FDA Approval for World's First Insulin Pump with Real-time Continuous Glucose Monitoring," Apr. 13, 2006, 3 pages.
Patent Abstracts of Japan, vol. 1999, No. 04, and JP 11 010036, Apr. 30, 1999 and Jan. 19, 1999, Toray Ind. Inc., 6 pages.
Walsh et al., "Guidelines for Insulin Dosing in Continuous Subcutaneious Insulin Infusion Using New Formulas from a Retrospective Study of Individuals with Optimal Glucose Levels", J. Diabetes Science and Technology, Sep. 2010, 4(5):8 pages.
Walsh et al., "Guidelines for Optimal Bolus Calculator Settings in Adults", J. Diabetes Science and Technology, Jan. 2011, 5(1):7 pages.
Supplementary European Search Report in Application No. EP 14807248, dated Feb. 28, 2017, 7 pages.

* cited by examiner

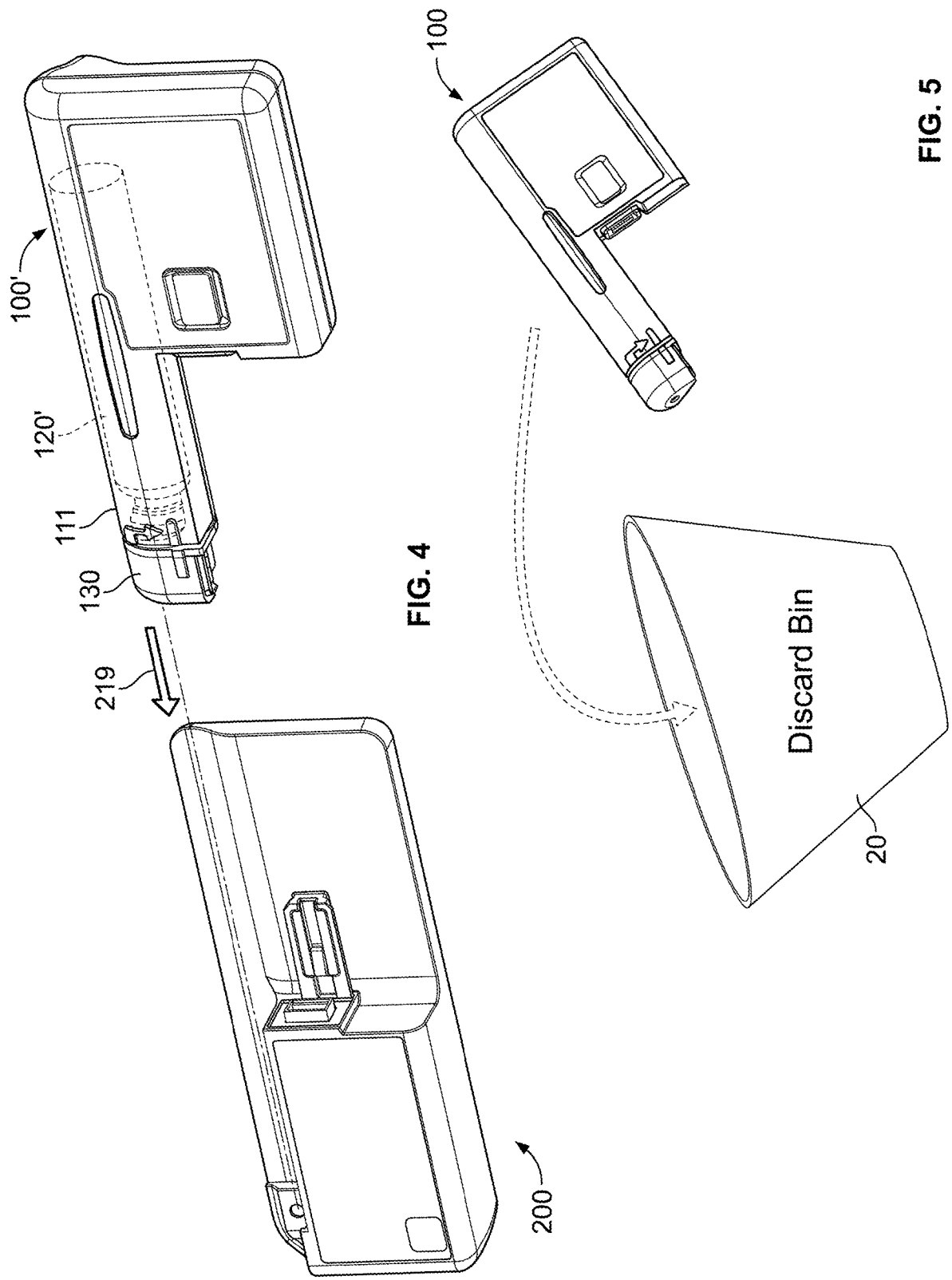

INFUSION PUMP SYSTEM AND METHOD

CROSS-REFERENCE TO RELATED APPLICATION

This application is a division of U.S. application Ser. No. 13/908,513, filed Jun. 3, 2013, the entire contents of which are hereby incorporated by reference.

TECHNICAL FIELD

This document relates to an infusion pump system, such as a portable infusion pump system for dispensing a medicine.

BACKGROUND

Pump devices are commonly used to deliver one or more fluids to a targeted individual. For example, a medical infusion pump device may be used to deliver a medicine to a patient as part of a medical treatment. The medicine that is delivered by the infusion pump device can depend on the condition of the patient and the desired treatment plan. For example, infusion pump devices have been used to deliver insulin to the vasculature of diabetes patients so as to regulate blood-glucose levels.

Infusion pump devices often need to deliver medicine in accurately controlled dosages. Over-dosages and under-dosages of medicine can be detrimental to patients. For example, an infusion pump device that delivers an over-dosage or under-dosage of insulin to a diabetes patient can significantly affect the blood-glucose level of the patient.

In some circumstances, the ability of an infusion pump to deliver an accurately controlled dosage can be negatively affected if the pump device has experienced moisture ingress. For example, an infusion pump device may be damaged by moisture within the pump casing as a result of submersion in water or other water exposure over a particular period of time.

SUMMARY

Some embodiments of an infusion pump system may be configured to detect when moisture inside a housing of the infusion pump system is greater than or equal to a threshold level. In particular embodiments, the infusion pump system can be equipped with a moisture detection system. In such circumstances, the moisture detection system includes a moisture detector that can sense presence level of moisture inside a pump housing at or above the threshold level (also referred to herein as a "high moisture level"). When the moisture detector provided herein senses a high moisture level, the infusion pump system can initiate one or more patient safety countermeasures. In some circumstances, the patient safety counter measures can include, for example, one or more of disabling medicine delivery by the pump device, emitting an alarm to the user, and prompting the user to perform a number of remedial actions.

In particular embodiments described herein, a portable infusion pump system may include a pump device and a controller device. The pump device may include a pump housing that defines a space to receive a medicine, a drive system positioned in the pump housing to dispense the medicine from the pump device when the medicine is received in the space of the pump housing, and a moisture detector positioned in the pump housing. Optionally, the moisture detector can provide an indication of a moisture level in the pump housing. The controller device may optionally be removably attachable to the pump housing so as to electrically connect with the pump device. The controller device may house control circuitry configured to communicate with the drive system positioned in the pump housing to control dispensation of the medicine from the pump device.

In some embodiments, a medical infusion pump system may include a portable housing defining a space to receive a medicine. The system may also include a pump drive system to dispense medicine from the portable housing when the medicine is received in the space. Further, the system may include control circuitry that electrically communicates with the pump drive system to control dispensation of the medicine from the portable housing when the medicine is received in the space. Also, the system may include a moisture detector. Optionally, the moisture detector may be positioned in the portable housing and in electrical communication with the control circuitry. In these circumstances, the moisture detector may provide an indication of a moisture level in the portable housing.

Some embodiments described herein may include a method of controlling a portable infusion pump system. The method may include sensing that a moisture detector positioned in a portable infusion pump system indicates a moisture level greater than or equal to a predetermined threshold level. The method may optionally include, in response to the sensing that the moisture detector indicates the aforementioned moisture level, disabling a pump drive system housed in the portable infusion pump system.

Some or all of the embodiments described herein may provide one or more of the following advantages. First, some embodiments of the infusion pump system may be configured to detect when the pump system has a moisture level inside a pump housing (e.g., an internal moisture level) that could potentially damage the system or cause an over-dosage or under-dosage of medicine to the user. Second, some embodiments of the infusion pump system may initiate user safety countermeasures upon detection that the system has an internal moisture level that is greater than or equal to a threshold level. Third, certain embodiments of an infusion pump system may prevent the use of a damaged system that may have some potential for delivery of an improper medicine dosage if used. Fourth, some embodiments of an infusion pump system may include a moisture detector that can be implemented at a cost that facilitates its usage in a disposable pump unit. Fifth, the infusion pump system may be configured to be portable, wearable, and (in some circumstances) concealable. For example, a user can conveniently wear the infusion pump system on the user's skin under clothing or can carry the pump system in the user's pocket (or other portable location) while receiving the medicine dispensed from the pump device.

The details of one or more embodiments of the invention are set forth in the accompanying drawings and the description below. Other features, objects, and advantages of the invention will be apparent from the description and drawings, and from the claims.

DESCRIPTION OF DRAWINGS

FIGS. 4-5 are perspective views of the pump device of FIGS. 1-2 being discarded and the controller device of FIGS. 1-2 being reused with a new pump device.

DETAILED DESCRIPTION OF ILLUSTRATIVE EMBODIMENTS

Figure 1:
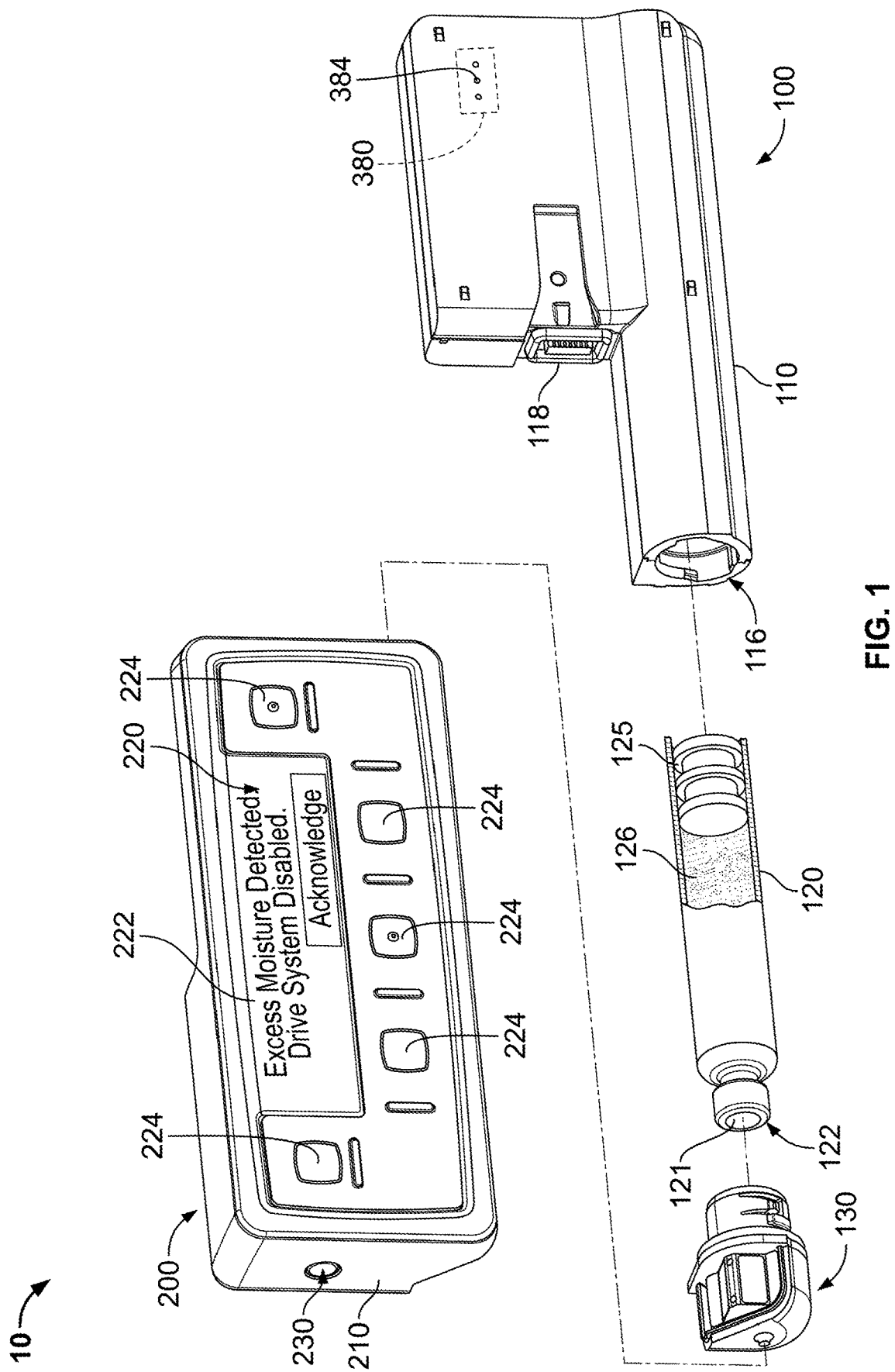
FIG. 1 is an exploded perspective view of an infusion pump system in accordance with some embodiments.

Referring to FIG. 1, an infusion pump system 10 can include a pump device 100 and a controller device 200 that communicates with the pump device 100. The pump device 100 in this embodiment includes a housing structure 110 that defines a cavity 116 in which a fluid cartridge 120 can be received. The pump device 100 also can include a cap device 130 to retain the fluid cartridge 120 in the cavity 116 of the housing structure 110. The pump device 100 can include a drive system that advances a plunger 125 in the fluid cartridge 120 so as to dispense fluid 126 therefrom.

In some embodiments, the controller device 200 communicates with the pump device 100 to control the operation of the drive system. When the controller device 200, the pump device 100 (including the cap device 130), and the fluid cartridge 120 are assembled together, the user can (in some embodiments) conveniently wear the infusion pump system 10 on the user's skin under clothing, in a pouch clipped at the waist (e.g., similar to a cell phone pouch), or in the user's pocket while receiving the fluid dispensed from the pump device 100. Optionally, the controller device 200 may be configured as a reusable component that provides electronics and a user interface to control the operation of the pump device 100. In such circumstances, the pump device 100 can be a disposable component that is disposed of after a single use. For example, as described in more detail below in connection with FIGS. 4-5, the pump device 100 can be a "one time use" component that is thrown away after the fluid cartridge 120 therein is exhausted. Thereafter, the user can removably attach a new pump device 100' (having a new medicine cartridge 120') to the reusable controller device 200 for the dispensation of fluid from a new fluid cartridge 120'. Accordingly, the user is permitted to reuse the controller device 200 (which may include complex or valuable electronics, as well as a rechargeable battery) while disposing of the relatively low-cost pump device 100 after each use. Such a pump system 10 can provide enhanced user safety as a new pump device 100' (and drive system therein) is employed with each new fluid cartridge 120'.

Briefly, in use, the pump device 100 is configured to removably attach to the controller device 200 in a manner that provides a secure fitting, an overall compact size, and a reliable electrical connection that is resistant to water migration. For example, as described in more detail below in connection with FIGS. 1-5, the controller device 200 can include a housing 210 having a number of features that mate with complementary features of the pump housing 110. In such circumstances, the controller device 200 can removably attach with the pump device 100 in a generally side-by-side configuration. The compact size permits the infusion pump system 10 to be discrete and portable (as described below in connection with FIG. 3). Moreover, at least one of the pump device 100 or the controller device 200 can include a release member that facilitates an easy-to-use detachment and replacement process.

As described in more detail below in connection with FIGS. 7-9, some embodiments of the infusion pump system 10 can include one or more internal moisture detection systems that each include a moisture detector, such as the moisture detector 380 arranged inside the housing structure 110 of the pump device 100. In particular embodiments, a second moisture detection system can be located within the controller housing structure 210, in addition to the moisture detector 380 within the pump device 100. In alternative embodiments, just the controller device 200 contains a moisture detection system.

The moisture detector 380 can be configured to sense if the pump device 100 has an internal moisture level that is greater than or equal to a threshold level. The threshold level can be established below the moisture level that could cause the pump device 100 to potentially malfunction. In that manner, the moisture detector 380 can be used to detect a potentially detrimental moisture level and to disable further operations of the potentially malfunctioning pump device 100 in a proactive manner. Such malfunctions might include an error to the pump drive system that causes the delivery of an over-dosage or under-dosage of medicine to the user, or a complete failure of the pump device 100 to operate.

A high moisture level may occur, for example, by moisture migration into the pump device 100 after a submersion in liquid at a particular threshold depth or greater and for a particular threshold duration of time. As described in more detail below, the housing structure 110 can include one or more miniature weep holes 384 or micro-pores through the wall of the housing structure 110 at a position adjacent to the moisture detector 380 such that a liquid ingress through the holes 384 will be detected by the moisture detector 380. Preferably, the size of the miniature holes 384 are selected so that water can only seep inside the pump housing if the pump device 100 is exposed to water of a particular time duration (e.g., a direct spray of water over a period of minutes (e.g., three minutes or greater), submersion underwater for a period of minutes (e.g., 1 meter depth underwater for thirty minutes or greater), or the like). (The size of the holes 384 in FIGS. 1 and 7 is enlarged for purposes of illustration only, and the holes 384 may be substantially smaller in some embodiments.) In another example scenario, if the housing structure 110 has been damaged thereby compromising the housing's resistance to water migration, water could potentially seep into the housing structure 110 from sources such as rain, water splashes, and the like and be detected by the moisture detector 380.

As described in more detail below in connection with FIGS. 2 and 8, when the pump device 100 and the controller device 200 are electrically coupled, the moisture detector 380 can be in electrical communication with control circuitry housed in the controller device 200. In the illustrated embodiments, the electrical coupling can result from mechanical engagement between the pump device 100 and the controller device 200. In alternative embodiments, wireless electrical communications may be established between the pump device 100 and the controller device 200 (or functional equivalents thereto) with or without mechanical engagement or a direct electrical connection.

In response to the initial establishment of electrical communications between the pump device 100 and the controller device 200, the circuit housed in the controller device 200 can interrogate the moisture detector 380 to ascertain whether a high moisture level exists within the pump device 100. If a high moisture level is determined to be present, the controller device 200 can initiate appropriate user safety countermeasures. If no high moisture level is detected, the pump system 10 can proceed with normal operations. During normal operations, the control circuitry housed in the controller device 200 can continue to periodically interrogate the moisture detector 380 at regular intervals, and if it is subsequently determined that a high moisture level is present the controller device 200 can respond by initiating appropriate user safety countermeasures.

Referring again to FIG. 1, the pump system 10 can be a medical infusion pump system that is configured to controllably dispense a medicine from the cartridge 120. As such, the fluid cartridge 120 can contain a medicine 126 to be infused into the tissue or vasculature of a targeted individual, such as a human or animal patient. For example, the pump device 100 can be adapted to receive a medicine cartridge 120 in the form of a carpule that is preloaded with insulin or another medicine for use in the treatment of Diabetes (e.g., Byetta®, Symlin®, or others). Such a cartridge 120 may be supplied, for example, by Eli Lilly and Co. of Indianapolis, Ind. Other examples of medicines that can be contained in the fluid cartridge 120 include: pain relief drugs, hormone therapy, blood pressure treatments, anti-emetics, osteoporosis treatments, or other injectable medicines. The fluid cartridge 120 may have other configurations. For example, the fluid cartridge 120 may comprise a reservoir that is integral with the pump housing structure 110 (e.g., the fluid cartridge 120 can be defined by one or more walls of the pump housing structure 110 that surround a plunger to define a reservoir in which the medicine is injected or otherwise received).

In some embodiments, the pump device 100 can include one or more structures that interfere with the removal of the medicine cartridge 120 after the medicine cartridge 120 is inserted into the cavity 116. For example, the pump housing structure 110 can include one or more retainer wings (not shown in FIG. 1) that at least partially extend into the cavity 116 to engage a portion of the medicine cartridge 120 when the medicine cartridge 120 is installed therein. Such a configuration may facilitate the "one-time-use" feature of the pump device 100. In some embodiments, the retainer wings can interfere with attempts to remove the medicine cartridge 120 from the pump device 100, thus ensuring that the pump device 100 will be discarded along with the medicine cartridge 120 after the medicine cartridge 120 is emptied, expired, or otherwise exhausted. In another example, the cap device 130 can be configured to irreversible attach to the pump body 110 so as to cover the opening of the cavity 116. For example, a head structure of the cap device 130 can be configured to turn so as to threadably engage the cap device 130 with a mating structure along an inner wall of the cavity 116, but the head structure may prevent the cap device from turning in the reverse direction so as to disengage the threads. Accordingly, the pump device 100 can operate in a tamper-resistant and safe manner because the pump device 100 can be designed with a predetermined life expectancy (e.g., the "one-time-use" feature in which the pump device is discarded after the medicine cartridge 120 is emptied, expired, or otherwise exhausted).

Still referring to FIG. 1, the controller device 200 can be removably attached to the pump device 100 so that the two components are mechanically mounted to one another in a fixed relationship. Such a mechanical mounting can form an electrical connection between the removable controller device 200 and the pump device 100. For example, the controller device 200 can be in electrical communication with a portion of a drive system (not shown in FIG. 1) of the pump device 100. As described in more detail below, the pump device 100 can include a drive system that causes controlled dispensation of the medicine or other fluid from the cartridge 120. In some embodiments, the drive system incrementally advances a piston rod (not shown in FIG. 1) longitudinally into the cartridge 120 so that the fluid is forced out of an output end 122. A septum 121 (FIG. 1) at the output end 122 of the fluid cartridge 120 can be pierced to permit fluid outflow when the cap device 130 is connected to the pump housing structure 110. For example, the cap device 130 may include a penetration needle that punctures the septum 121 during attachment of the cap device to the housing structure 110. Thus, when the pump device 100 and the controller device 200 are attached and thereby electrically connected, the controller device 200 communicates electronic control signals via a hardwire-connection (e.g., electrical contacts or the like) to the drive system or other components of the pump device 100. In response to the electrical control signals from the controller device 200, the drive system of the pump device 100 causes medicine to incrementally dispense from the medicine cartridge 120. Power signals, such as signals from the rechargeable battery 245 (refer to FIG. 6) of the controller device 200 and from the power source 310 (refer to FIG. 7) of the pump device 100 may also be passed between the controller device 200 and the pump device 100.

As shown in FIG. 1, the pump device 100 can include an electrical connector 118 (e.g., having conductive pads, pins, and the like) that is exposed to the controller device 200 and that mates with a complementary electrical connector (refer to connector 218 in FIG. 2) on the adjacent face of the controller device 200. The electrical connectors 118 and 218 provide the electrical communication between the control circuitry (refer, for example, to FIG. 6) housed in the controller device 200 and at least a portion of the drive system or other components of the pump device 100. For example, in some embodiments, the electrical connectors 118 and 218 can permit the transmission of electrical control signals to the pump device 100 and the reception of feedback signals (e.g., sensor signals) from particular components within the pump device 100. The electrical connectors 118 and 218 may similarly facilitate transmission of one or more power signals from the rechargeable battery pack 245 to the pump device 100, where the signals may be used to provide power to components of the pump device 100, or to transmit one or more power signals from the power source 310 to the controller device, where the signals may be used to charge the rechargeable battery 245 or to power components of the controller device 200.

Still referring to FIG. 1, the controller device 200 can include a user interface 220 that permits a user to monitor the operation of the pump device 100. In some embodiments, the user interface 220 can include a display device 222 and one or more user-selectable buttons (e.g., several buttons 224 are shown in the embodiment of FIG. 1). The display device 222 can include an active area in which numerals, text, symbols, images, or a combination thereof can be displayed. For example, the display device 222 can be used to communicate a number of settings or menu options for the infusion pump system 10. In this embodiment, the user may press one or more of the buttons to shuffle through a number of menus or program screens that show particular settings and data (e.g., review data that shows the medicine dispensing rate, the total amount of medicine dispensed in a given time period, the amount of medicine scheduled to be dispensed at a particular time or date, the approximate amount of medicine remaining in the cartridge 120, or the like). In some embodiments, the user can adjust the settings or otherwise program the controller device 200 by pressing one or more buttons of the user interface 220. For example, in embodiments of the infusion pump system 10 configured to dispense insulin, the user may press one or more of the buttons to change the dispensation rate of insulin or to request that a bolus of insulin be dispensed immediately or at a scheduled, later time. In some implementations, the display device 222 may also be used to communicate information regarding remaining battery life.

Accordingly, when the controller device 200 is connected to the pump device 100, the user can be provided with the opportunity to readily monitor the infusion pump operation by simply viewing the user interface 220 of the controller device 200 connected to the pump device 100. Such monitoring capabilities may provide comfort to a user who may have urgent questions about the current operation of the pump device 100. Also, in these embodiments, there may be no need for the user to carry and operate a separate module to monitor the operation of the pump device 100, thereby simplifying the monitoring process and reducing the number of devices that must be carried by the user. If a need arises in which the user desires to monitor the operation of the pump device 100 or to adjust the settings of the pump system 10 (e.g., to request a bolus amount of medicine), the user can readily operate the user interface 220 of the controller device 200, which is removably attached to the pump device 100, without the requirement of locating and operating a separate monitoring module.

The controller device 200 can also be equipped with an inspection light device 230. The inspection light device 230 can provide the user with a tool to illuminate and inspect a targeted location. For example, the inspection light device 230 can be directed at the infusion site on the user's skin to verify that the infusion set is properly embedded, or the inspection light device 230 can be directed at the pump device 100 to illuminate the cavity 116 or other areas.

The inspection light device 230 can also be used to notify the user to an alert condition of the pump system 10. For example, as described further in reference to FIG. 9 below, the inspection light device 230 can be activated when the moisture detector has detected a moisture level greater than or equal to the threshold level. An activation of the inspection light device 230 can thereby provide a visual notification (as an alternative to, or in addition to, the visual notification provided on the display device 222) to the user that attention to the pump system 10 is warranted.

Figure 2:
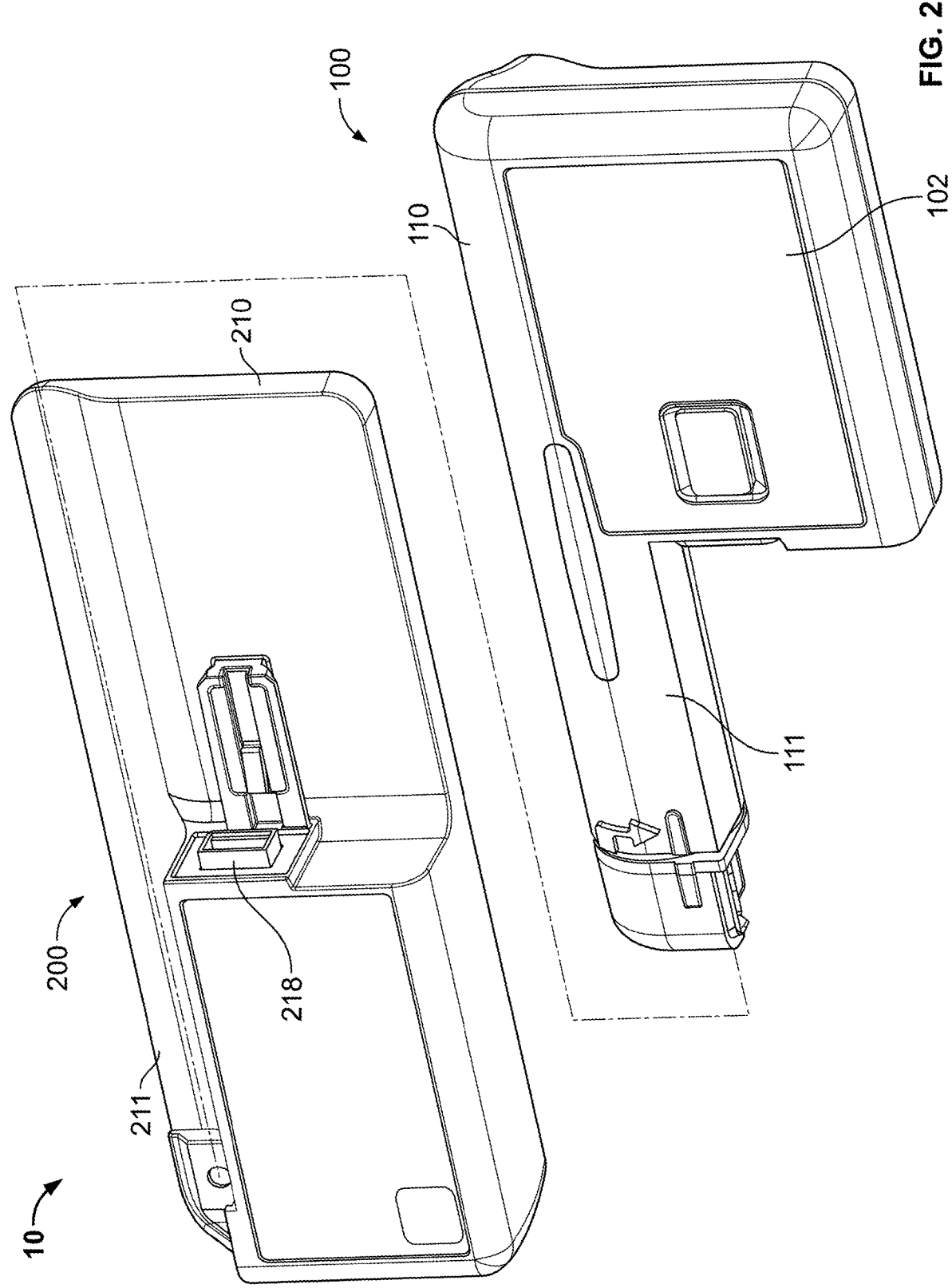
FIG. 2 is a perspective view of the infusion pump system of FIG. 1 in a detached state.

Referring now to FIG. 2, when the infusion pump system 10 operates, the controller device 200 can be removably attached to the pump device 100 in a side-by-side arrangement. For example, the pump device 100 may be moved in a longitudinal direction (e.g., refer to direction 219 in FIG. 4) toward the controller device 200 until the complementary features connect and secure the separate components in the side-by-side arrangement. The controller device 200 can include a controller housing structure 210 having a number of features that are configured to mate with complementary features of the pump housing structure 110 so as to form a releasable mechanical connection. For example, the pump housing structure 110 can include a barrel 111 that mates with a complementary barrel channel 211 of the controller housing 210. In various implementations, the pump device 100 and the controller device 200 can be mounted to one another so that the assembled system 10 is resistant to water migration both into the pump housing structure 110 and the controller housing structure 210. Such a configuration can also provide water-resistant protection for the electrical connection between the pump device 100 and the controller device 200. Thus, the sensitive internal components in the controller device 200 and the pump device 100 may be reliably protected from water migration if the user encounters some amount of water (e.g., rain, incidental splashing, and the like) while using the pump system 10. However, in the event of a more substantial exposure to water, such as a submersion over an extended period of time, the moisture detector 380 as described herein can protect the user from a pump system 10 malfunction that may result from water ingress into the pump housing 110 (or into the controller housing 210 if the controller device 200 is also equipped with a moisture detector similar to the detector 380 (FIG. 8)).

Figure 3:
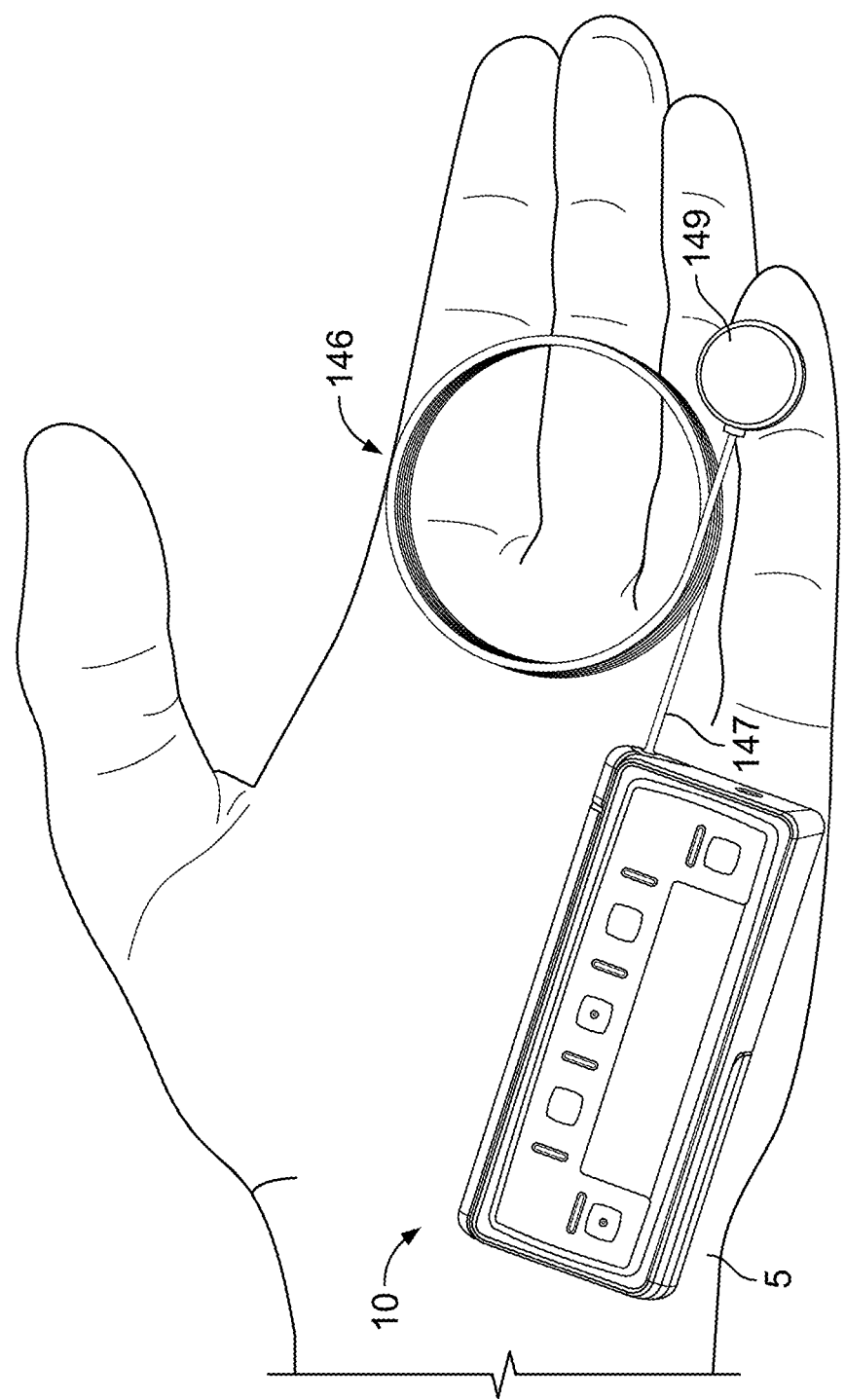
FIG. 3 is a perspective view of an infusion pump system, in accordance with some embodiments.

Referring to FIG. 3, the infusion pump system 10 can be configured to be portable and can be wearable and concealable. For example, a user can conveniently wear the infusion pump system 10 on the user's skin (e.g., skin adhesive) underneath the user's clothing or carry the pump device 100 in the user's pocket (or other portable location) while receiving the medicine dispensed from the pump device 100. The pump system 10 is shown in FIG. 3 as being held in a user's hand 5 so as to illustrate an exemplary size of the system 10 in accordance with some embodiments. This embodiment of the infusion pump system 10 is compact so that the user can wear the portable infusion pump system 10 (e.g., in the user's pocket, connected to a belt clip, adhered to the user's skin, or the like) without the need for carrying and operating a separate module. In such embodiments, the cap device 130 of the pump device 100 can be configured to mate with an infusion set 146. In general, the infusion set 146 can be a tubing system that connects the infusion pump system 10 to the tissue or vasculature of the user (e.g., to deliver medicine into the tissue or vasculature under the user's skin). The infusion set 146 can include a flexible tube 147 that extends from the pump device 100 to a subcutaneous cannula 149 that may be retained by a skin adhesive patch (not shown) that secures the subcutaneous cannula 149 to the infusion site. The skin adhesive patch can retain the infusion cannula 149 in fluid communication with the tissue or vasculature of the user so that the medicine dispensed through the tube 147 passes through the cannula 149 and into the user's body. The cap device 130 can provide fluid communication between the output end 122 (FIG. 1) of the medicine cartridge 120 and the tube 147 of the infusion set 146.

In some embodiments, the infusion pump system 10 can be pocket-sized so that the pump device 100 and controller device 200 can be worn in the user's pocket or in another portion of the user's clothing. In some circumstances, the user may desire to wear the pump system 10 in a more discrete manner. Accordingly, the user can pass the tube 147 from the pocket, under the user's clothing, and to the infusion site where the adhesive patch can be positioned. As such, the pump system 10 can be used to deliver medicine to the tissues or vasculature of the user in a portable, concealable, and discrete manner.

In some embodiments, the infusion pump system 10 can be configured to adhere to the user's skin directly at the location in which the skin is penetrated for medicine infusion. For example, a rear surface 102 (FIG. 2) of the pump device 100 can include a skin adhesive patch so that the pump device 100 can be physically adhered to the skin of the user at a particular location. In these embodiments, the cap device 130 can have a configuration in which medicine passes directly from the cap device 130 into an infusion cannula 149 that is penetrated into the user's skin. In some examples, the user can temporarily detach the controller device 200 (while the pump device 100 remains adhered to the skin) so as to view and interact with the user interface 220.

Referring now to FIGS. 4-5, the infusion pump system 10 can be operated such that the pump device 100 is a disposable, non-reusable component while the controller device 200 is a reusable component. In these circumstances, the pump device 100 may be configured as a "one-time-use" device that is discarded after the medicine cartridge is emptied, expired, or otherwise exhausted. Thus, in some embodiments, the pump device 100 can be designed to have an expected operational life of about 1 day to about 30 days, about 1 day to about 20 days, about 1 to about 14 days, or about 1 day to about 7 days-depending on the volume of medicine in the cartridge 120, the dispensation patterns that are selected for the individual user, and other factors. For example, a medicine cartridge 120 containing insulin can have an expected usage life of about 7 days after the cartridge is removed from a refrigerated state and the septum 121 is punctured. In some circumstances, the dispensation pattern selected by the user can cause the insulin to be emptied from the medicine cartridge 120 before the 7-day period. If the insulin is not emptied from the medicine cartridge 120 after the 7-day period, the remaining insulin can become expired sometime thereafter. In either case, the pump device 100 and the medicine cartridge 120 therein can be collectively discarded after exhaustion of the medicine cartridge 120 (e.g., after being emptied, expired, or otherwise not available for use).

The controller device 200, however, may be reused with subsequent new pump devices 100' and new medicine cartridges 120'. As such, the control circuitry, the user interface components, the rechargeable battery pack 245, and other components that may have relatively higher manufacturing costs can be reused over a longer period of time. For example, in some embodiments, the controller device 200 can be designed to have an expected operational life of about 1 year to about 7 years, about 2 years to about 6 years, or about 3 years to about 5 years—depending on a number of factors including the usage conditions for the individual user. Accordingly, the user can be permitted to reuse the controller device 200 (which can include complex or valuable electronics, and a rechargeable battery pack) while disposing of the relatively low-cost pump device 100 after each use. Such a pump system 10 can provide enhanced user safety as a new pump device 100' (and drive system therein) is employed with each new medicine cartridge 120'.

Referring to FIGS. 4-5, the same controller device 200 can be reused with a new pump device 100' having a new medicine cartridge 120' retained therein, and the previously used pump device 100, including the exhausted medicine cartridge, can be discarded in a discard bin 20. The new pump device 100' (FIG. 4) can have a similar appearance, form factor, and operation as the previously used pump device 100, and thus the new pump device 100' can be readily attached to the controller device 200 for controlled dispensation of medicine from the new medicine cartridge 120'. In some embodiments, the user can prepare the new pump device 100' for use with the controller device 200. For example, the user may insert the new medicine cartridge 120' in the cavity 116 of the new pump device 100' and then join the cap device 130 to the pump housing to retain the new medicine cartridge 120' therein (refer, for example, to FIG. 1). Although the tubing 147 of the infusion set 146 is not shown in FIG. 4, it should be understood that the tubing 147 can be attached to the cap device 130 prior to the cap device 130 being joined with the housing 110. For example, a new infusion set 146 can be connected to the cap device 130 so that the tubing 147 can be primed (e.g., a selected function of the pump device 100 controlled by the controller device 200) before attaching the cannula's adhesive patch to the user's skin. As shown in FIG. 4, the new medicine cartridge 120' may be filled with medicine such that the plunger 125 is not viewable through the barrel 111.

The new pump device 100' can be removably attached to the controller device 200 to assemble into the infusion pump system 10 for delivery of medicine to the user. As previously described, the guided motion in the longitudinal direction 219 provides the user with a convenient "one-movement" process to attach the pump device 100' and the controller device 200. For example, the user can readily slide the pump device 100' and the controller device 200 toward one another in a single movement (e.g., in the longitudinal direction 219) that causes both a physical connection and an electrical connection. Thus, the infusion pump system 10 can permit users to readily join the pump device 100' and the controller device 200 without compound or otherwise difficult hand movements—a feature that can be particularly beneficial to child users or to elderly users.

Figure 6:
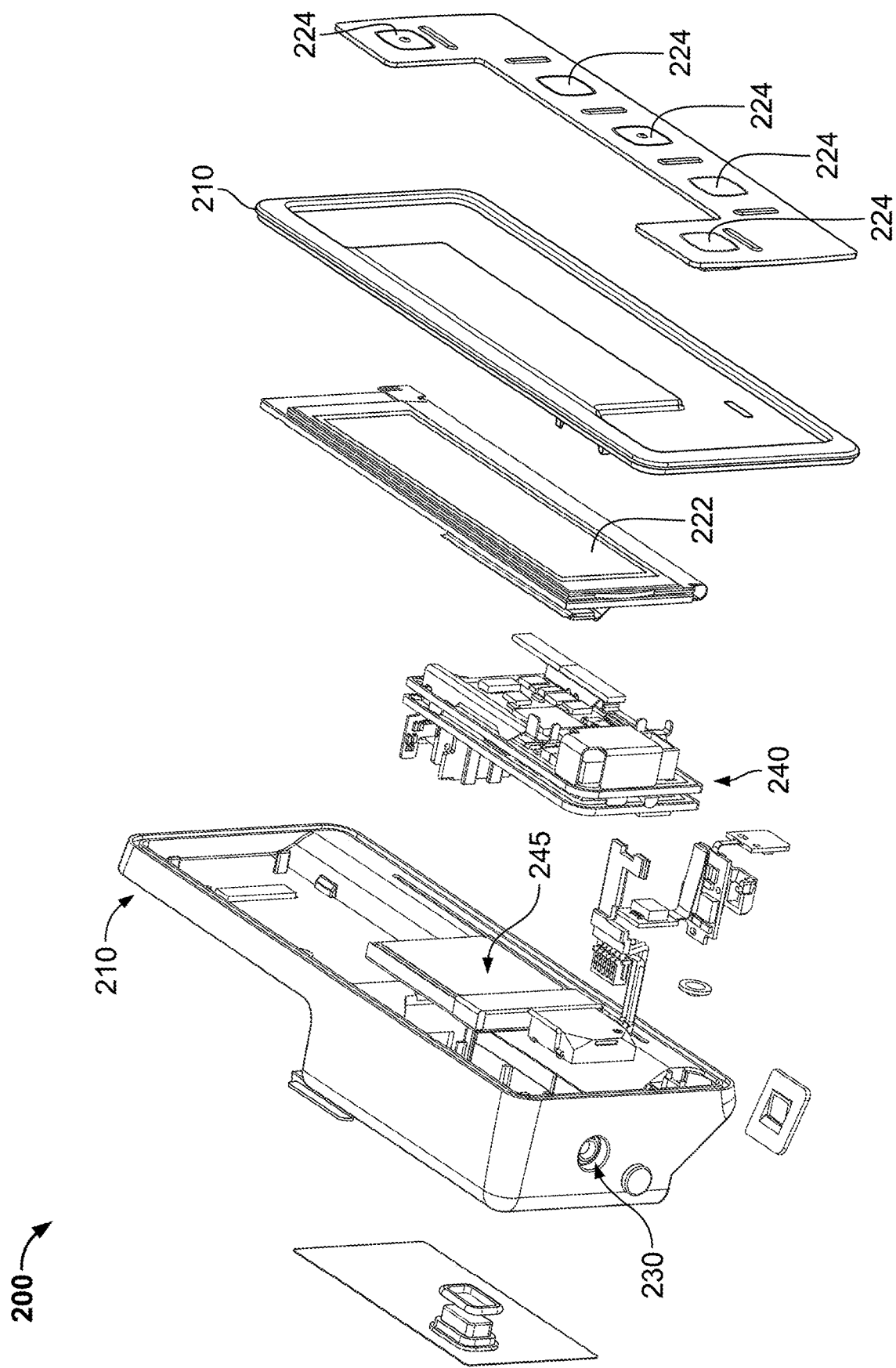
FIG. 6 is an exploded perspective view of a controller device for an infusion pump system, in accordance with some embodiments.

Referring now to FIG. 6, the controller device 200 (shown in an exploded view) houses a number of components that can be reused with a series of successive pump devices 100. In particular, the controller device 200 can include controller circuitry 240 and a rechargeable battery pack 245, each arranged in the controller housing 210. As described above, rechargeable battery pack 245 may provide electrical energy to components of controller circuitry 240, other components of the controller device (e.g., a display device 222 and other user interface components, sensors, or the like), or to components of the pump device 100. Controller circuitry 240 may be configured to communicate control or power signals to the drive system of the pump device 100, or to receive power or feedback signals from the pump device 100.

In some embodiments, the controller device 200 can house a moisture detector (not shown) that is similar to the moisture detector 380 (FIG. 8) in the pump housing 110, which can be employed to detect high levels of moisture within the controller housing 210. If a moisture level at or above a threshold level is detected inside the controller housing 210, the infusion pump system 10 can initiate user safety countermeasures as described herein.

Still referring to FIG. 6, the user interface 220 of the controller device 200 can include input components and/or output components that are electrically connected to the controller circuitry 240. For example, the user interface 220 can include the display device 222 having an active area that outputs information to a user and buttons 224 that the user can use to provide input. Here, the display device 222 can be used to communicate a number of settings or menu options for the infusion pump system 10. In some embodiments, the controller circuitry 240 can receive input commands from a user's button selections and thereby cause the display device 222 to output a number of menus or program screens that show particular settings and data (e.g., review data that shows the medicine dispensing rate, the total amount of medicine dispensed in a given time period, the amount of medicine scheduled to be dispensed at a particular time or date, the approximate amount of medicine remaining the cartridge 120, the amount of battery life remaining, or the like). The controller circuitry 240 can be programmable to cause the controller circuitry 240 to change any one of a number of settings for the infusion pump system 10. For example, the user may provide one or more instructions to adjust a number of settings for the operation of the infusion pump system 10. Such settings may be stored in one or more memory devices arranged in the controller circuitry 240.

As shown in FIG. 6, the infusion pump system 10 can be equipped with the inspection light device 230 to conveniently aid in visual inspection processes. For example, visual inspection and possible change of the infusion set 146 may be required in less than optimal conditions, including low-light conditions. Likewise, visual inspection of the pump housing cavity 116 (and the medicine cartridge 120 therein) may be required in low-light conditions. The user interface 220 of the controller device 200 can include an illuminated display screen 222 to facilitate the user's view of the display screen 222, but the inspection light device 230 provides a dedicated light source for illuminating targeted sites external to the controller device 200, for providing an alert notification, or a combination thereof.

The inspection light device 230 can include one or more user triggered light sources that are positioned to direct illumination at targeted objects outside of the pump system 10 or at components of the pump device 100. In the embodiment depicted in FIG. 6, the light source is arranged on the controller device 200. Such an arrangement provides close proximity to the control circuitry 240 housed in the controller device 200, thereby permitting the light source of the inspection light device 230 to be electrically connected to the control circuitry. In other embodiments, could be arranged on the pump device 100 or on both the controller device 200 and the pump device 100.

The inspection light device 230 can also be used to provide a visual notification to the user in the event of an alert or alarm condition. For example, as described further in reference to FIG. 9, the inspection light device 230 can be activated in response to detection by the moisture detection system of a moisture level within the housing(s) of the pump system 10 that is at or above a threshold value at which a potential malfunction of the pump system 10 may be caused.

In some optional embodiments, the controller circuitry 240 can include a cable connector (e.g., a USB connection port or another data cable port) that is accessible on an external portion of the controller housing 210. As such, a cable can be connected to the controller circuitry 240 to upload data or program settings to the controller circuitry or to download data from the controller circuitry. For example, historical data of medicine delivery can be downloaded from the controller circuitry 240 (via the cable connector) to a computer system of a physician or a user for purposes of analysis and program adjustments. Optionally, the data cable can also provide recharging power.

Figure 7:
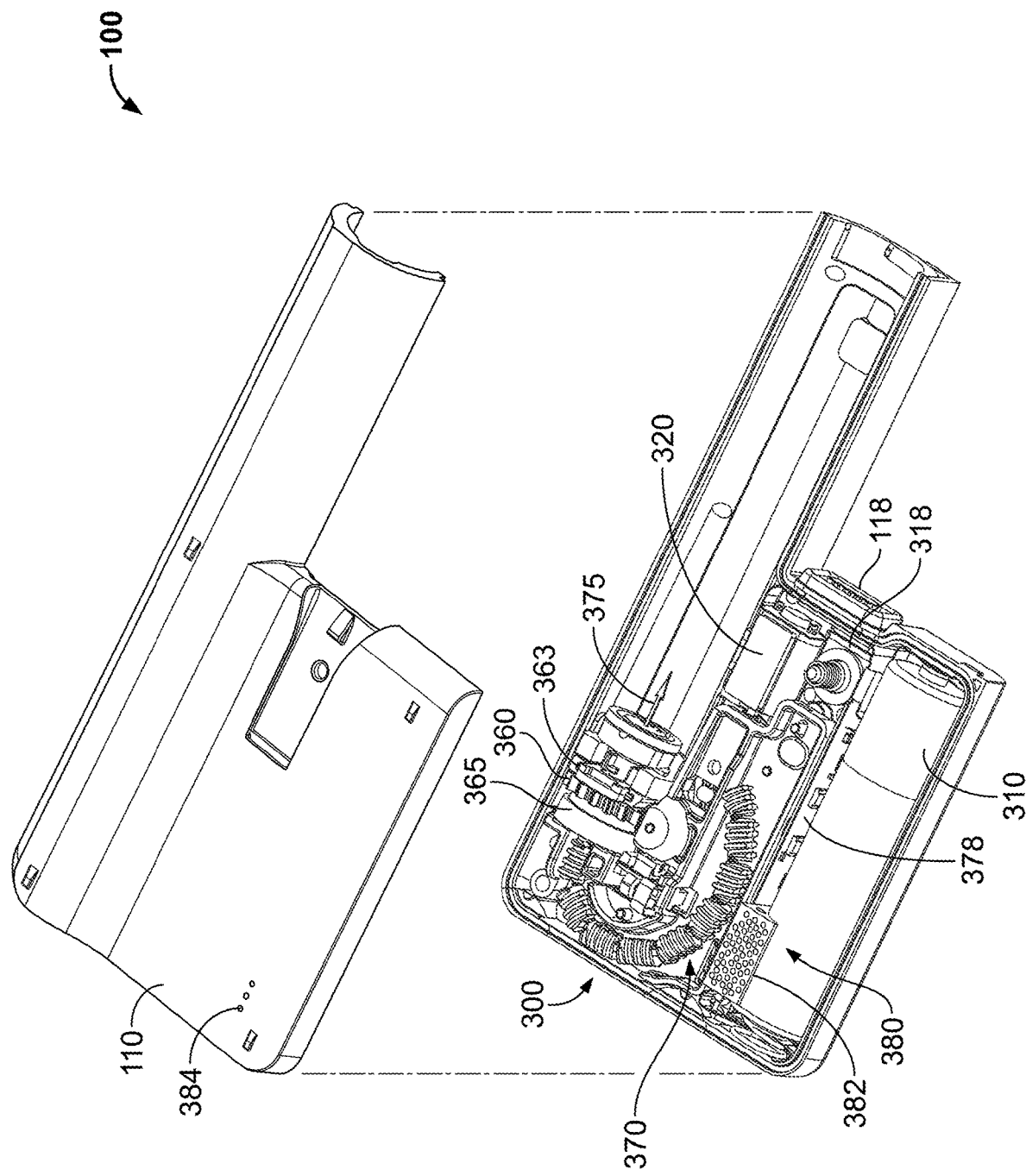
FIG. 7 is an exploded perspective view of a pump device for an infusion pump system, in accordance with some embodiments.

Referring now to FIG. 7, the pump device 100 can include a drive system 300 that is controlled by the controller device 200. As described in more detail below, the drive system 300 can incrementally dispense fluid in a controlled manner from cartridge 120 inserted into the pump device 100. Also, the pump device 100 may include a connector circuit 318 to facilitate the transfer of signals to and from the electrical connector 118. In some implementations, the connector circuit 318 in the pump device 100 may include a memory device that can store data regarding the pump device 100 and its operational history. As previously described, the electrical connector 118 of the pump device 100 can mate with the connector 218 (FIG. 2) of the controller device 200 so that electrical communication can occur between the pump device 100 and the controller device 200. In some embodiments, the connector circuit 318 can operate as a passageway to transmit electrical control signals from the controller circuitry 240 of the controller device 200 to the drive system 300. The connector circuit 318 can also operate as a passageway for the electrical power from a power source 310 housed in the pump device 100 to pass to the controller device 200 for recharging of the rechargeable battery 245. Furthermore, the connector circuit 318 can operate as a passageway for feedback signals from the drive system 300 to the controller circuitry 240 of the controller device 200.

In this embodiment, the pump device 100 houses the drive system 300 and the power source 310. For example, the power source 310 may comprise an alkaline battery cell, such as a 1.5 Volt "AAA" alkaline battery cell, which is contained in a dedicated space of the pump housing structure 110. The power source 310 may be capable of transmitting electrical energy to the controller device 200 when the pump device 100 is attached to the controller device 200, via connectors 118 and 218 as described above. For example, the power source 310 may be used to charge the rechargeable battery pack 245 when the pump device 100 is attached to the controller device 200. In some embodiments, the power source 310 is used to provide energy to the drive system 300 of the pump device 100, and also to electronic components of the controller device 200. In particular embodiments, the power source 310 may provide the energy to power all aspects of the infusion pump system 10. In some alternative embodiments, the rechargeable battery 245 housed in the controller 200 may provide the energy to power all aspects of the infusion pump system 10. In other embodiments, the rechargeable battery 245 and the power source 310 may each be responsible for powering particular aspects of the infusion pump system 10. In further embodiments, the rechargeable battery 245 may provide the energy to supplement the energy provided by the power source 310 to power aspects of the infusion pump system.

Still referring to FIG. 7, in some embodiments, the drive system 300 may include a number of components, such as an electrically powered actuator (e.g., reversible motor 320 or the like), a drive wheel 360, a bearing 365, a flexible piston rod 370, a piston rod guide 363, and a plunger engagement device 375. In this embodiment, the reversible motor 320 drives a gear system (not shown in FIG. 7) to cause the rotation of the drive wheel 360 that is coupled with the bearing 365. The drive wheel 360 may include a central aperture with an internal thread pattern, which mates with an external thread pattern on the flexible piston rod 370. The interface of the threaded portions of the drive wheel 360 and flexible piston rod 370 may be used to transmit force from the drive wheel to the piston rod 370. Accordingly, in the embodiment of FIG. 7, the drive wheel 360 is the driver while the flexible piston rod 370 is the driven member. As further described below, the rotation of the drive wheel 360 can drive the flexible piston rod 370 forward in a linear longitudinal direction.

Figure 8:
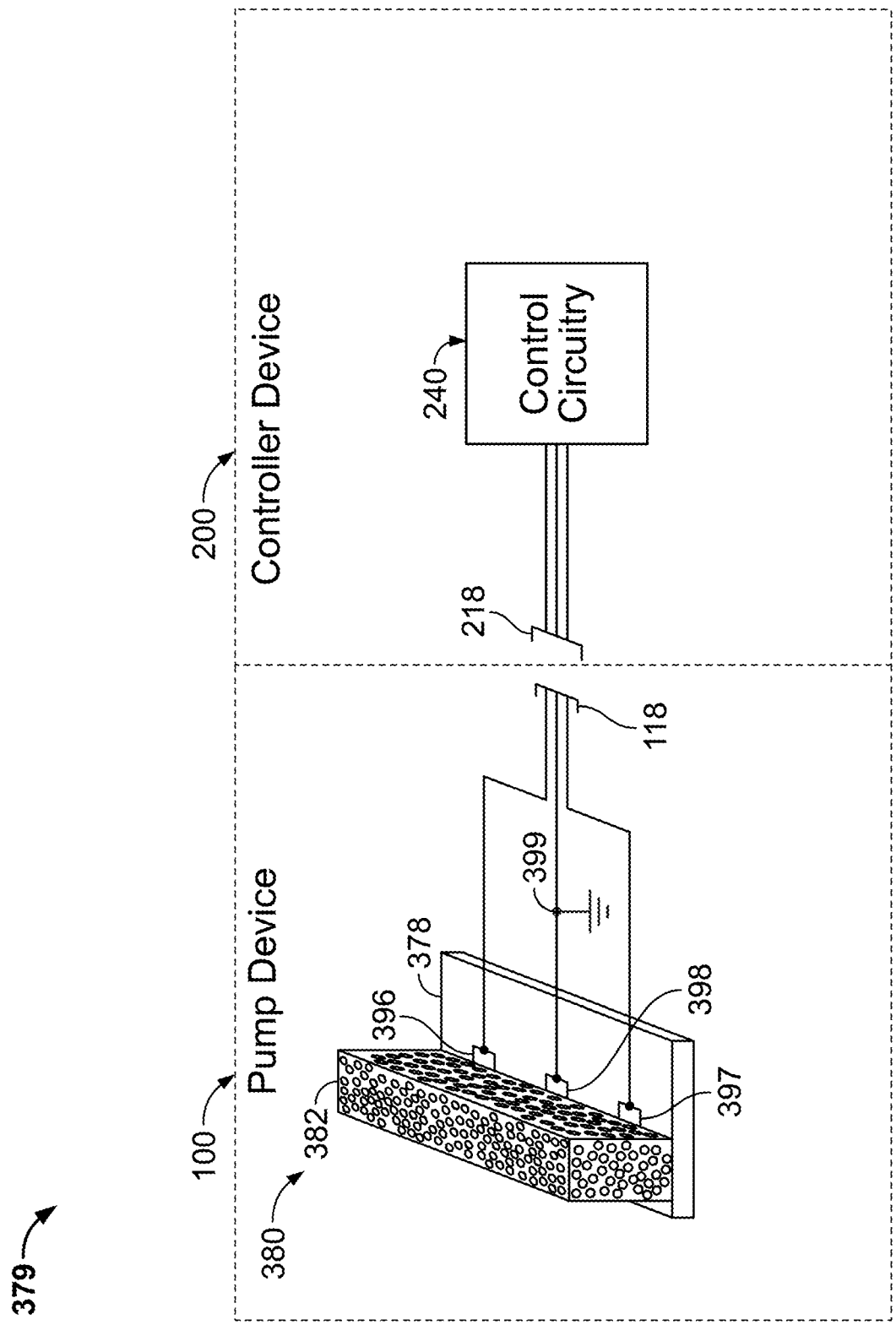
FIG. 8 is a schematic of moisture detection system, in accordance with some embodiments.

Referring now to FIGS. 7 and 8, the pump device 100 (or, in some embodiments, the controller device 200, or both devices 100 and 200) can also house a moisture detector, such as the example moisture detector 380 described further below. As previously described, moisture detection systems can detect a moisture level within the infusion pump system 10 that is greater than or equal to a moisture threshold level. The moisture threshold level can be established at or below the lowest level of moisture that may induce a malfunction of the infusion pump system 10. Moisture detection systems can thereby sense and forewarn the user of moisture levels that have the potential to induce damage to the infusion pump system 10, including the type of damage that could cause over-dosage or under-dosage of medicine to the user, in a proactive manner. In other words, when a moisture level at or above the threshold level is detected by the moisture detection system, the controller device 200 can initiate appropriate user safety countermeasures (some examples of such countermeasures are described in connection with FIG. 9).

A variety of types and configurations of moisture detectors are envisioned within the scope of this document. For example, in some embodiments, the moisture detector for the moisture detection system can include one or more electrochemical-based moisture sensor devices. Such electrochemical-based moisture sensor devices may in some cases be capable of distinguishing different types of moisture, such as water versus insulin (which could leak from a damaged insulin cartridge, for example). The infusion pump system 10 may in such cases be configured to provide the user with alarm messages that provide specific information as to the type of moisture detected (e.g., insulin, water, or some other type of moisture). In other embodiments, the moisture detector for the moisture detection system can include various types of humidity sensors, such as capacitive sensors for example. In still other embodiments, the moisture detector can be an electrical resistance-type moisture sensor. In particular embodiments, two or more moisture detectors can be included as part of a moisture detection system. For example, multiple moisture detectors can be located at multiple locations near the peripheral seal of the pump housing 110, the controller device housing 210, or both housings 110 and 210. In other words, moisture detectors can be implemented in either or both of the pump device 100 and the controller device 200, or in a monolithic pump device (as described in reference to FIG. 10).

In this embodiment, the example moisture detector 380 is an electrical resistance-type moisture sensor that utilizes the relationship between the moisture content of a generally insulative substance and the electrical resistance of the insulative substance. In particular, electrical resistance-type moisture sensors operate on the principle that an insulative substance generally has a high resistance to the flow of electricity, and that the substance's resistance is lessened when the substance absorbs moisture. When the insulative substance's resistance is lessened by the moisture, it can conduct a flow of electricity and the flow of electricity can be detected by a monitoring circuit. As a result of detecting a flow of electricity through the insulative substance, the monitoring circuit can ascertain that the amount of moisture in the insulative substance is at or above a threshold level amount of moisture.

Providing further general description of electrical resistance-type moisture sensors, electrical resistance-type moisture sensors can include two or more electrical connections that are connected to the insulative substance. The two or more electrical connections are spaced apart from each other on the insulative substance. One of the electrical connections can receive an electrical potential in relation to another electrical connection. When the insulative substance is dry, little or no electrical current can flow between the electrical connections. However, when the insulative substance absorbs moisture, some electrical current can be conducted between the electrical connections, and that conductance of electricity can be detected by a monitoring circuit (FIG. 8). The amount of electricity conducted will be related to the amount of moisture in the insulative substance. Using these principles, an electrical resistance-type moisture sensor can be used to detect the presence of moisture at or above a threshold level amount of moisture within the infusion pump system 10.

Still referring to FIGS. 7 and 8, the example moisture detection system 379 includes at least the moisture detector 380 and a detection software component of the controller circuitry 240. In this embodiment, the moisture detector 380 includes an absorbent element 382 and a circuit board 378 housed inside the pump housing 110. The absorbent element 382 can comprise one or more of a variety of materials. In general, the absorbent element 382 can be made from any suitable material that provides the desired characteristics of being electrically insulative (when dry) and liquid absorbent. For instance, the example moisture detector 380 includes an absorbent element 382 that is a foam material. A hydrophilic sponge material such as AQUAZONE® WD available from Foamex Innovations of Media, Pa. is one example of a suitable foam material. Other example materials are the medical foam materials from Rynel, Inc. of Wiscasset, Me.

In this embodiment, at least portions of the absorbent element 382 and the circuit board 378 are in physical contact with each other. For example, three conductive pads 396, 397, and 398 on the circuit board 378 are each in contact with portions of the absorbent element 382. The conductive pads 396, 397, and 398, being in contact with portions of the absorbent element 382, are thereby arranged to be in electrical communication with each other via conductance of electricity through the absorbent element 382. In some embodiments pins, probes, nodes, and the like are used as alternatives to the conductive pads 396, 397, and 398.

Some or all of the pads 396, 397, and 398 are individually in electrical communication with the controller circuitry 240. That is, in the embodiment shown in FIG. 8, the pads 396, 397, and 398 are hardwired (via the electrical connectors 118 and 218) to the controller circuitry 240. In alternative embodiments, some or all of the pads 396, 397, and 398 can be in wireless communication with the controller circuitry 240. By virtue of the electrical communication between the pads 396, 397, and 398 and the controller circuitry 240, the controller circuitry 240 can monitor the electrical status of the pads 396, 397, and 398. As described further below, by monitoring the electrical status of the pads 396 and 397 the controller circuitry 240 can ascertain whether or not a high moisture level exists within the pump device 100.

In addition to the connections from the pads 396, 397, and 398 to the controller circuitry 240, the pads 396, 397, and 398 may also connected to other points on the electrical systems within the pump device 100. For example, in some embodiments, pads 396 and 397 can be individually connected to separate voltage sources on the circuit board 378, and pad 398 is connected to ground 399 (common). In this example, when an electrical component (e.g., a pad or a voltage source) has an electrical charge, it can be said that the component is "high." Conversely, when an electrical component does not have an electrical charge it can be said that the component is "low." Hereafter, the terms "high" and "low" may be used to indicate an existence or absence of electrical potential in regards to the pads 396 and 397 and the voltage sources that are connected to the pads 396 and 397. In this particular example, the infusion pump system 10 may operate such that either one or both of the voltage sources that are connected to pads 396 and 397 are always high. That is, at least one pad 396 or 397 always receives an electrical potential from its respective voltage source when the infusion pump system 10 is in operation. In a first operative scenario, pad 396 receives electrical potential and pad 397 does not receive electrical potential. In a second operative scenario, pad 397 receives electrical potential and pad 396 does not receive electrical potential. In a third operative scenario, both pads 396 and 297 receive electrical potential. During operation of the infusion pump system 10, the electrical potential of the voltage sources connected to pads 396 and 397 can be switched between any of the aforementioned three scenarios. But at all times during normal operation of the infusion pump system 10, at least one of the voltage sources connected to pads 396 and 397 is high. In contrast, pad 398 is always low because pad 398 is electrically connected to ground 399.

Referring to FIG. 8, when pump device 100 is in the normal state, the absorbent element 382 is substantially dry or contains less than a threshold level amount of moisture. In that condition, little or substantially no electricity is conducted through the insulative absorbent element 382. Consequently, when pads 396 and 397 are supplied with an electrical potential, the pads 396 and 397 will maintain the electrical potential. That holds true because there is no conductive path for the electrical potential to flow away from the pads 396 and 397 when the absorbent element 382 contains less than a threshold level amount of moisture. Therefore, in this normal state, either one or both pads 396 and 397 will be high. The controller circuitry 240 will detect that at least one pad 396 or 397 is high, and the controller circuitry 240 will interpret the status of the pump device 100 as normal (as not having a high moisture level). Indeed, as long as the controller circuitry 240 detects that at least one of the pads 396 or 397 is high, the controller circuitry 240 will allow the normal operations of the infusion pump system 10 to continue.

However, when the absorbent element 382 absorbs moisture at a level that is greater than a threshold level amount of moisture, the electrical resistance of the absorbent element 382 is decreased, and the absorbent element 382 may then conduct electricity more readily. In this embodiment, the extent of the decrease in resistance of the absorbent element 382 is generally proportional to the amount of moisture absorbed by the absorbent element 382. This decrease in resistance of the absorbent element 382 enables the absorbent element 382 to effectively provide an electrical connection from pads 396 and 397 to pad 398 (ground), thereby causing both of the pads 397 and 397 to provide a low signal (e.g., connected to ground). The absorbent element 382 provides this type of conductive path between the pads 396, 397, and 398 when the absorbent element 382 receives at least a threshold level amount of moisture (e.g., such as a particular amount of moisture seeping into the pump housing via the micro-pores 384 (FIG. 7).

For the aforementioned reasons, when the absorbent element 382 has at least a threshold level amount of moisture content, both pads 396 and 397 will be low. Thus, when the detection software component of the controller circuitry 240 interrogates the moisture detector 380, it will in turn detect that both pads 396 and 397 are low. As a result of detecting that both pads 396 and 397 are low, the controller circuitry 240 will initiate one or more user safety countermeasures as described further herein.

Figure 9:
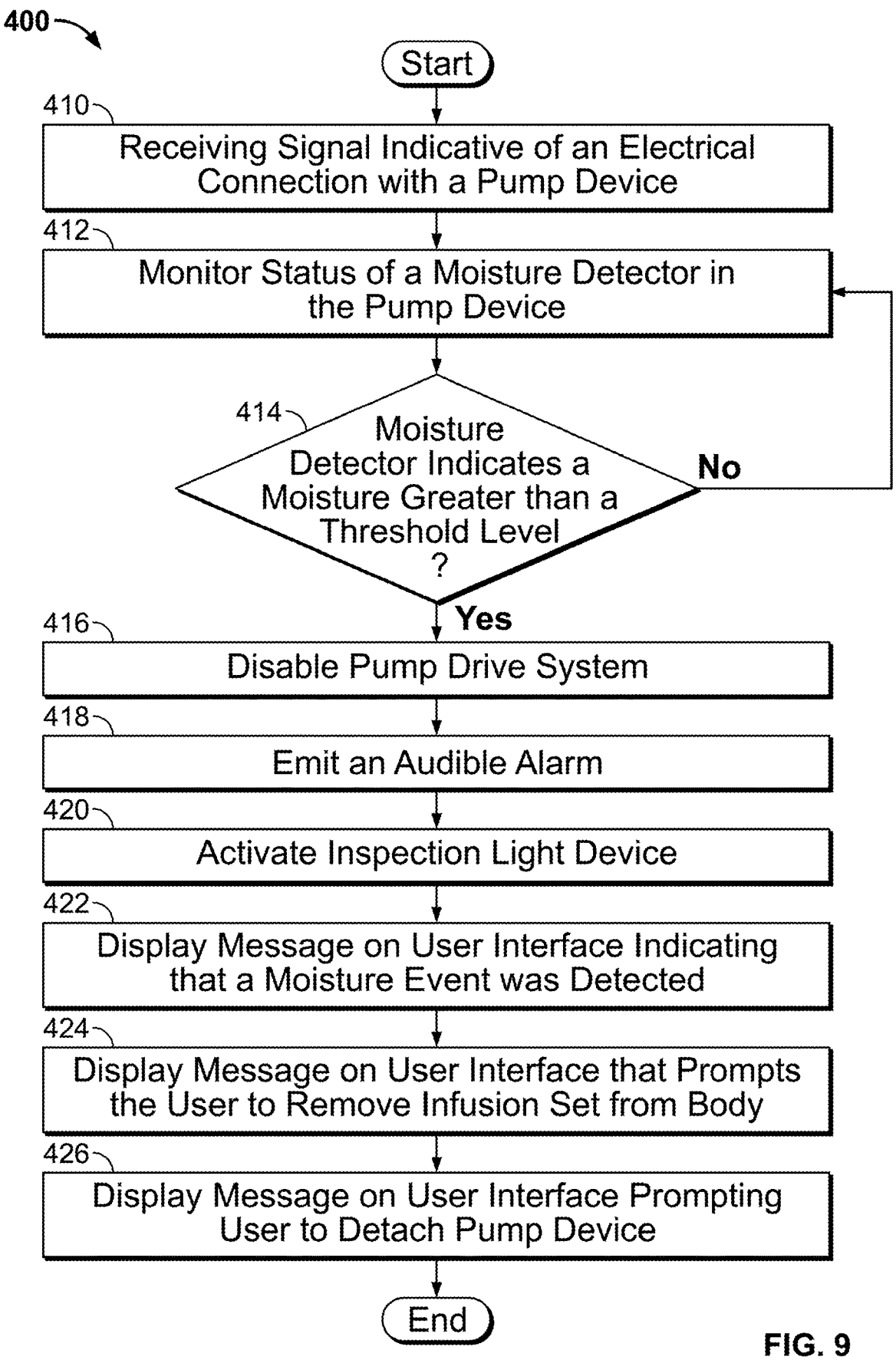
FIG. 9 is a flowchart describing a process of using a moisture detection system of an infusion pump system in accordance with some embodiments.

Referring now to FIG. 9, a controller of an infusion pump system that includes a moisture detector can implement a process 400 of detecting a moisture event. Such a process 400, for example, can be implemented by the controller circuitry 240 in the controller device 200 of the infusion pump system 10 (FIG. 1). Alternatively, some operations of the process 400 could be implemented in an infusion pump device in which the controller and the pump drive system are integrated into a single housing (such as the embodiment of FIG. 10).

In operation 410, the controller circuitry can receive an electrical signal indicating that a pump device is in electrical communication (hard wired or wirelessly) with the controller device. For example, in the embodiments in which controller device 200 is separately housed from the pump device 100, the two components can be electrically connected via the connectors 118 and 218. As such, the signal can be a voltage from power source 310 that is detected by controller circuitry 240 when the pump device 100 is electrically connected to the controller device 200.

In operation 412, the controller circuitry monitors the status of the moisture detector. Such a monitoring operation can include periodic samplings of the moisture detector by the controller circuitry. For example, in the embodiments described above, the controller circuitry 240 may sample the moisture detector 380 prior to each time the controller circuitry 240 initiates a dispensation of medicine from the infusion pump system 10. In other embodiments, the controller circuitry 240 may sample the moisture detector 380 on a periodic time basis, such as about every 1, 2, 5, or 10 minutes, for example. If the moisture detection circuit indicates that the pump system is in a "high moisture level" mode, the monitoring operation 412 will detect that the signal(s) from the moisture detector differ from the signal(s) when in the "normal" mode.

In operation 414, the controller device determines if the moisture detector indicates a moisture level greater than or equal to a threshold level. For example, in the embodiment shown in FIGS. 7 and 8, the moisture detector 380 can indicate the presence of excessive moisture in the absorbent element 382, thereby causing the moisture detection system 386 to ascertain the "high moisture level" detected mode. If the moisture detector does not indicate that a high moisture level event occurred, the process 400 returns to the monitoring operation 412.

Still referring to FIG. 9, if the moisture detector indicates a moisture level greater than or equal to a threshold level, the controller device can respond according to some or all of the operations 416, 418, 420, 422, 424, and 426.

In operation 416, in response to the controller device's determination that the moisture detector system indicates the pump device 100 has an internal moisture level at or above the moisture threshold level (e.g., the "high moisture level" mode has been sensed), the controller device can act to disable the pump drive system. For purposes of safety, the pump system 10 may immediately stop the delivery of medicine to the user of the system. As described above, the cessation of medicine delivery can be an appropriate user safety precaution because a moisture level at or above the moisture threshold level can potentially damage the pump system's drive mechanisms or electronics, whereby an over-dosage or under-dosage could occur. As an alternative to automatically disabling the pump drive system, the process 400 can instead include an operation in which the user is prompt to confirm/approve that the pump drive system can be disabled. In addition to (or in as an alternative to) disabling the pump drive system, the controller device can initiate further user safety countermeasures as described in the next steps of operation process 400.

In operation 418, the controller device can emit an audible alarm in response to a determination of a moisture level at or above the threshold level. The purpose of the audible alarm is to alert the user to the issue that the pump system 10 is not operating normally and requires attention. The audible alarm can be emitted before, after, or simultaneously with the operation 416 of disabling the drive system.

Optionally, in operation 420, a separate light device of the pump system can be activated to provide a visible alarm (in addition to the audible alarm of operation 418). For example, the inspection light device 230 of pump system 10 can be activated to provide a visual notification to the user to the issue that the pump system 10 is not operating normally and requires attention.

In operation 422, the controller device can display a message to indicate that a moisture event was detected in response to a determination of a moisture level at or above the threshold level. For example, the user interface display screen 222 on the controller device 200 can display a short textual message to alert the user. The message can provide the user with an explanation of the reason for the audible and visual alarms. Further, the message can provide the user with an explanation that the pump drive system was automatically disabled.

In operation 424, the controller device can display a message prompting the user to remove the infusion set from the user's body. For example, the user interface display screen 222 on the controller device 200 can display the message prompting the user to remove the infusion set from the user's body. This message can be provided in order to assist the user with taking the proper actions to prevent an over dispensation of medicine to the user's body as a result of the detected high moisture level.

Optionally, in operation 426, the controller device can display a message prompting the user to detach the pump device from the controller device. For example, the user interface display screen 222 on the controller device 200 can display a message prompting the user to detach the pump device 100 from the controller device 200. In order to resume use of the pump system 10, the pump device 100 that has a moisture level at or above the moisture threshold level will need to be removed from the controller device 200 so that a new pump device, such as pump device 100' (refer to FIGS. 4 and 5) can be coupled with the controller device 200. This message assists the user to take the proper actions in response to the activation of the moisture detection system, and to proceed towards resumption of the use of a properly functioning pump system 10.

Figure 10:
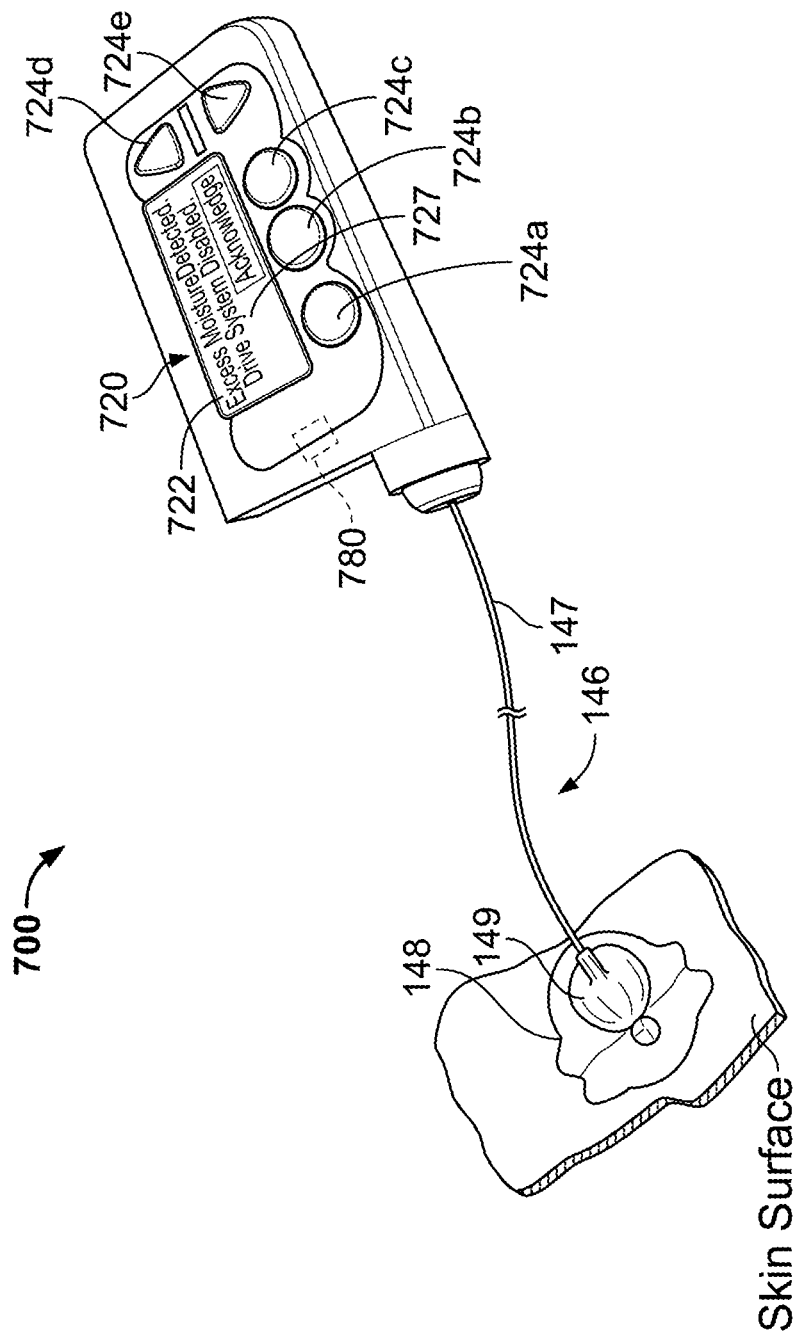
FIG. 10 is a perspective view of an alternative infusion pump system in accordance with some embodiments Like reference symbols in the various drawings indicate like elements.

Referring now to FIG. 10, some embodiments of a portable infusion pump system 700 having a moisture detector 780 can employ a reusable pump apparatus (rather than a disposable pump device as previously described). In such circumstances, the infusion pump system 700 may comprise a reusable device that houses the control circuitry and the pump drive system within a single housing construct. In the particular embodiment depicted in FIG. 10, the pump system 700 comprises a reusable pump device that houses both the controller circuitry and the pump drive system. Similar to previously described embodiments, the pump system 700 can include a housing structure that defines a cavity in which a medicine cartridge can be received (not shown in FIG. 10; refer for example to cartridge 120 in FIG. 1). For example, the pump system 700 can be adapted to receive a medicine cartridge in the form of a carpule that is preloaded with insulin or another medicine. The pump drive system can act upon the fluid cartridge to controllably dispense medicine through an infusion set 146 and into the user's tissue or vasculature. In this embodiment, the user can wear the portable pump system 700 on the user's skin under clothing or in the user's pocket while receiving the medicine dispensed through the infusion set 146.

Similar to previously described embodiments, the infusion pump system 700 may include the moisture detector 780 that can detect a moisture level greater than or equal to a moisture threshold level. The threshold level can be established below the moisture level that may cause the infusion pump system 700 to potentially fail or to cause an over-dosage or under-dosage of medicine to the user. Such a moisture level may occur, for example, by moisture seepage into the infusion pump system 700. Optionally, as previously described, the pump housing structure can include one or more miniature weep holes or micro-pores (not shown in FIG. 10) through the outer wall of the housing structure at a position adjacent to the moisture detector 780 such that a liquid ingress through the holes will be detected by the moisture detector 780. Preferably, the size of the miniature holes are selected so that water can only seep inside the pump housing if the pump system 700 is exposed to water of a particular time duration (e.g., a direct spray of water over a period of minutes (e.g., three minutes or greater), submersion underwater for a period of minutes (e.g., 1 meter depth underwater for thirty minutes or greater), or the like).

Accordingly, the moisture detector 780 of the infusion pump system 700 can be constructed like any of the embodiments described above, such as the electrical resistance-type moisture sensor embodiment depicted in FIGS. 7 and 8. This type of moisture detection system may communicate with the control circuitry of the system 700 so that the infusion pump system 700 can initiate appropriate user safety countermeasures if the detected moisture level was greater than or equal to the predetermined threshold level.

In some embodiments, the moisture detector circuitry for use with the moisture detector 780 can be similar to the moisture detection system 386 described in reference to FIG. 8, but with several adaptations. For example, because the infusion pump system 700 has a single housing, the moisture detector circuit may not necessarily communicate via the electrical connectors 118 and 218. Consequently, the moisture detection circuit used with the moisture detector 780 in the infusion pump system 700 may optionally be a simplified version of the moisture detection system 386 depicted in FIG. 8.

Still referring to FIG. 10, the user interface 720 of the pump system 700 includes a display device 722 and one or more user-selectable buttons 724*a-e*. The display device 722 can include an active area in which numerals, text, symbols, images, or a combination thereof can be displayed (as shown, for example, in FIG. 10). For example, the display device 722 can be used to communicate to the user that a moisture event has been detected and the drive system has been disabled (similar to the process described in reference to FIG. 9). Also, the display device 722 can be used to communicate a number of settings or menu options for the infusion pump system 700. For example, the display device 722 can be used to communicate medicinal delivery information 727, such as the basal delivery rate, a bolus dosage, a historical record of medicine delivered, the amount of medicine remaining in the cartridge, or the like. In another example, the display device 722 can be used to communicate time and date information, which can be used by the user to determine dosage schedules, bolus delivery times, meal times, or the like. Accordingly, the user may press one or more of the buttons 724a, 724b, 724c, 724d, and 724e to shuffle through a number of menus or program screens that show particular settings and data (e.g., review data that shows the medicine dispensing rate, the total amount of medicine dispensed in a given time period, the amount of medicine scheduled to be dispensed at a particular time or date, the approximate amount of medicine remaining in the cartridge 120, or the like). Also, the user can adjust the settings or otherwise program the pump system 700 by pressing one or more buttons 724a, 724b, 724c, 724d, and 724e of the user interface 420. Thus, the user can contemporaneously monitor the operation of the pump system 700, including any messages pertaining to the moisture detection system from the same user interface 720.

A number of embodiments of the invention have been described. Nevertheless, it will be understood that various modifications may be made without departing from the spirit and scope of the invention. Accordingly, other embodiments are within the scope of the following claims.

What is claimed is:

1. A medical infusion pump system, comprising:
    a portable housing defining a space to receive a medicine;
    a pump drive system to dispense medicine from the portable housing when the medicine is received in the space;
    control circuitry that electrically communicates with the pump drive system to control dispensation of the medicine from the portable housing when the medicine is received in the space; and
    hydrophilic foam material positioned in the portable housing and in electrical communication with the control circuitry, the control circuitry being adapted to detect absorption of moisture into the hydrophilic foam material,
    wherein the portable housing defines one or more liquid weep holes, and
    wherein the one or more liquid weep holes have a predefined size for passage of liquid through the outer wall the portable housing after a submersion in liquid at a particular threshold depth or greater and for a particular threshold duration of time.

2. The medical infusion pump system of claim 1, wherein the control circuitry is adapted to provide an indication of a moisture level in the portable housing.

3. The medical infusion pump system of claim 1, wherein the control circuitry is adapted to determine if a moisture level in the portable housing is greater than or equal to a predetermine non-zero threshold level of moisture.

4. The medical infusion pump system of claim 3, wherein the control circuitry is configured to initiate an alarm in response to the indication that the moisture level in the portable housing is greater than or equal to the predetermined non-zero threshold level of moisture.

5. The portable infusion pump system of claim 4, wherein, in response to the indication that the moisture level in the portable housing is greater than or equal to the predetermined non-zero threshold level of moisture, the control circuitry is configured to disable the drive system, activate an audible alarm, and display of one or more messages on a user interface display located on the portable housing.

6. The portable infusion pump system of claim 2, wherein the indication of the moisture level in the portable housing is based on a change in electrical resistance of the hydrophilic foam material.

7. The medical infusion pump system of claim 1, wherein the control circuitry is housed in a controller housing that is removably attachable to the portable housing.

8. The medical infusion pump system of claim 1, wherein the one or more liquid weep holes are positioned adjacent the hydrophilic foam material.

9. A method of controlling a portable infusion pump system, comprising:
    sensing that a hydrophilic foam material positioned in a portable infusion pump system has a change in an electrical resistance; and
    in response to the sensing that the change in an electrical resistance exceeds a threshold, disabling a pump drive system housed in the portable infusion pump system,
    wherein the portable infusion pump system defines one or more liquid weep holes, and
    wherein the one or more liquid weep holes have a predefined size for passage of liquid through an outer wall a pump housing of the portable infusion pump system after a submersion in liquid at a particular threshold depth or greater and for a particular threshold duration of time.

10. The method of claim 9, further comprising in response to the sensing that the change in an electrical resistance exceeds a threshold, emitting an audible alarm.

11. The method of claim 10, further comprising in response to the sensing that the change in an electrical resistance exceeds a threshold, displaying one or more alert messages on a user interface display of the portable infusion pump system.

12. The method of claim 11, further comprising in response to the sensing that the change in an electrical resistance exceeds a threshold, activating a light source of the portable infusion pump system that is different from the user interface display.

13. The method of claim 9, wherein the one or more liquid weep holes are positioned adjacent the hydrophilic foam material.

14. A medical infusion pump system, comprising:
    a portable housing defining a space to receive a medicine;
    a pump drive system to dispense medicine from the portable housing when the medicine is received in the space;
    control circuitry that electrically communicates with the pump drive system to control dispensation of the medicine from the portable housing when the medicine is received in the space;
    hydrophilic foam material positioned in the portable housing and in electrical communication with the control circuitry, the control circuitry being adapted to detect absorption of moisture into the hydrophilic foam material; and
    a plurality of conductive pads including a first conductive pad, a second conductive pad, and a third conductive pad that are each in electrical communication with the hydrophilic foam material,
    wherein the control circuitry is adapted to (i) detect, based on detected voltage levels of the first conductive pad and the third conductive pad, absorption of moisture to a first portion of the hydrophilic foam material and (ii) detect, based on detected voltage levels of the second conductive pad and the third conductive pad, absorption of moisture to a second portion of the hydrophilic foam material wherein the first conductive pad and the second conductive pad are connected to one or more voltage sources and the third conductive pad is connected to ground.

15. The medical infusion pump system of claim 14, wherein the portable housing defines one or more liquid weep holes positioned adjacent the hydrophilic foam material.

16. The medical infusion pump system of claim 15, wherein the one or more liquid weep holes have a predefined size for passage of liquid through the outer wall the portable housing after a submersion in liquid at a particular threshold depth or greater and for a particular threshold duration of time.

17. The medical infusion pump system of claim 14, wherein the first conductive pad, the second conductive pad, and the third conductive pad are respectively coupled to a first coupling portion, a second coupling portion, a third coupling portion of the hydrophilic foam material, and wherein the first portion of the hydrophilic foam material is between the first coupling portion and the third coupling portion of the hydrophilic foam material and the second portion of the hydrophilic foam material is between the second coupling portion and the third coupling portion of the hydrophilic foam material.

\* \* \* \* \*